US012427284B2

(12) United States Patent
Cosgriff-Hernandez et al.

(10) Patent No.: US 12,427,284 B2
(45) Date of Patent: Sep. 30, 2025

(54) ELECTRICALLY CONDUCTIVE HYDROGELS USABLE AS LEAD EXTENSIONS, APPARATUS FOR DELIVERY OF A HYDROGEL INTO THE VASCULATURE, AND METHODS OF TREATING VENTRICULAR ARRHYTHMIA WITH ELECTRICALLY CONDUCTIVE HYDROGELS INJECTED IN THE VENOUS SYSTEM

(71) Applicants: Texas Heart Institute, Houston, TX (US); Board of Regents, The University of Texas System, Austin, TX (US)

(72) Inventors: Elizabeth Cosgriff-Hernandez, Austin, TX (US); Mathews John, Houston, TX (US); Allison Post, Houston, TX (US); Mehdi Razavi, Houston, TX (US); Malgorzata Chwatko, Austin, TX (US); Ashley Rook, Kingwood, TX (US); Thomas Wilems, Austin, TX (US)

(73) Assignees: Texas Heart Institute, Houston, TX (US); Board of Regents, The University of Texas System, Austin, TX (US)

( * ) Notice: Subject to any disclaimer, the term of this patent is extended or adjusted under 35 U.S.C. 154(b) by 715 days.

(21) Appl. No.: 17/640,147

(22) PCT Filed: Sep. 4, 2020

(86) PCT No.: PCT/US2020/049532
§ 371 (c)(1),
(2) Date: Mar. 3, 2022

(87) PCT Pub. No.: WO2021/046441
PCT Pub. Date: Mar. 11, 2021

(65) Prior Publication Data
US 2022/0305234 A1  Sep. 29, 2022

Related U.S. Application Data

(60) Provisional application No. 62/896,480, filed on Sep. 5, 2019.

(51) Int. Cl.
| A61M 25/00 | (2006.01) |
| A61L 27/16 | (2006.01) |
| A61L 27/18 | (2006.01) |
| A61L 27/50 | (2006.01) |
| A61L 27/52 | (2006.01) |
| A61L 27/54 | (2006.01) |
| A61M 25/10 | (2013.01) |

(52) U.S. Cl.
CPC ......... *A61M 25/0068* (2013.01); *A61L 27/16* (2013.01); *A61L 27/18* (2013.01); *A61L 27/50* (2013.01); *A61L 27/52* (2013.01); *A61L 27/54* (2013.01); *A61M 25/0082* (2013.01); *A61L 2300/104* (2013.01); *A61L 2300/108* (2013.01); *A61L 2400/06* (2013.01); *A61M 2025/0073* (2013.01); *A61M 2025/1052* (2013.01)

(58) Field of Classification Search
None
See application file for complete search history.

(56) References Cited

U.S. PATENT DOCUMENTS

| 5,545,206 | A | 8/1996 | Carson |
| 5,800,685 | A | 9/1998 | Perrault |
| 6,312,421 | B1 | 11/2001 | Book |
| 2002/0161399 | A1 | 10/2002 | Cruise et al. |
| 2003/0229305 | A1 | 12/2003 | Levinson et al. |
| 2004/0267237 | A1 | 12/2004 | Sun et al. |
| 2006/0009801 | A1 | 1/2006 | Erin et al. |
| 2006/0100304 | A1 | 5/2006 | Vresilovic et al. |
| 2008/0109057 | A1 | 5/2008 | Calabria et al. |
| 2009/0171406 | A1 | 7/2009 | Foley et al. |
| 2009/0238815 | A1 | 9/2009 | Udipi et al. |

(Continued)

FOREIGN PATENT DOCUMENTS

| CN | 103325573 B | 9/2016 | |
| EP | 1107813 B1 * | 5/2006 | ....... A61B 17/00491 |

(Continued)

OTHER PUBLICATIONS

International Search Report and Written Opinion issued in application serial No. PCT/US2020/049532, mailed on Feb. 4, 2021, 23 pages.

(Continued)

*Primary Examiner* — H. Sarah Park
(74) *Attorney, Agent, or Firm* — Jonathan Pierce; Derek V. Forinash; Porter Hedges LLP

(57) ABSTRACT

A conductive hydrogel precursor solution cures after injection into the vasculature of the myocardium. The vasculature acts as a mold for the hydrogel and allows for a pacing signal to be conducted across the myocardium and not at a single point like traditional pacing leads. The catheter-based delivery can accurately place the hydrogels into the myocardial veins and can fill the venous tributaries. In situ crosslinking of the hydrogel precursor solution is achieved through several mechanisms, such as redox initiation by mixing a reducing reagent and oxidizing agent after injection. Conductivity is achieved by doping in conductive polymers or other conductive elements such as ionic species, metallic nanoparticles, or graphene nanoplatelets. To ensure long-term conductivity, hydrogel macromers may be synthesized without hydrolytically labile groups such as esters, and the conductive elements may be conjugated directly to the hydrogel matrix.

17 Claims, 20 Drawing Sheets

(56) References Cited

U.S. PATENT DOCUMENTS

| | | | |
|---|---|---|---|
| 2011/0087315 A1 | 4/2011 | Richardson-Burns et al. | |
| 2011/0245866 A1 | 10/2011 | Cassingham et al. | |
| 2014/0148791 A1* | 5/2014 | Barker, Jr. | A61B 17/12186 |
| | | | 604/82 |
| 2014/0187855 A1 | 7/2014 | Nagale et al. | |
| 2015/0203852 A1 | 7/2015 | Arora | |
| 2015/0366900 A1 | 12/2015 | Li | |
| 2017/0281869 A1 | 10/2017 | Kai et al. | |
| 2019/0031813 A1 | 1/2019 | Hong | |

FOREIGN PATENT DOCUMENTS

| | | | | |
|---|---|---|---|---|
| WO | 2002016453 A1 | 2/2002 | | |
| WO | WO-2018111949 A1 * | 6/2018 | ........... | A61B 5/0028 |
| WO | 2018134268 A1 | 7/2018 | | |
| WO | 2019018942 A1 | 1/2019 | | |

OTHER PUBLICATIONS

Imtiaz Hussain et al., Enhancing the mechanical propertis and self-healing efficiency of hydroxyethyl cellulose-based conductive hydrogels via supramolecular interactions, European Polymer Journal, May 25, 2018, pp. 85-94, vol. 105, Elsevier.

European Patent Office, Supplementary European Search Report issued in counterpart application serial No. 20860114.6, mailed Aug. 4, 2023, 9 pages.

CIPO, Examiner's report issued in counterpart Canadian application No. 3,150,246, mailed on Nov. 29, 2023, 5 pages.

Jose R. Garcia, Peter F. Campbell, Gautam Kumar, Jonathan J. Langberg, Liliana Cesar, Lanfang Wang, Andrés J. García, Rebecca D. Levit. "A minimally invasive, translational method to deliver hydrogels to the heart through the pericardial space." JACC: Basic to Translational Science. Oct. 2017. pp. 601-609, vol. 2, Issue 5, Elsevier.

Dashuai Zhu, Zhenhua Li, Ke Huang, Thomas G. Caranasos, Joseph S. Rossi & Ke Cheng. "Minimally invasive delivery of therapeutic agents by hydrogel injection into the pericardial cavity for cardiac repair." Nature Communications. Mar. 3, 2021. 10 pages, vol. 12, Article No. 1412, Springer.

Lee M, Kim MC, Lee JY. "Nanomaterial-Based Electrically Conductive Hydrogels for Cardiac Tissue Repair." Int J Nanomedicine. Dec. 9, 2022. pp. 6181-6200, vol. 17, Dovepress.

* cited by examiner

A) DELIVERY OF HYDROGEL PRECURSOR VIA DUAL LUMEN CATHETER

B) RAPID IN SITU CURE UPON MIXING OF TWO COMPONENTS DUE TO REDOX INITIATION

C) SUCCESSFUL MYOCARDIAL PACING

POLY (ETHYLENE GLYCOL) DIACRYLAMIDE (PEGDAA)

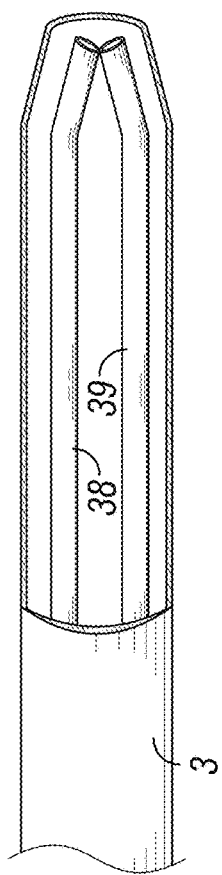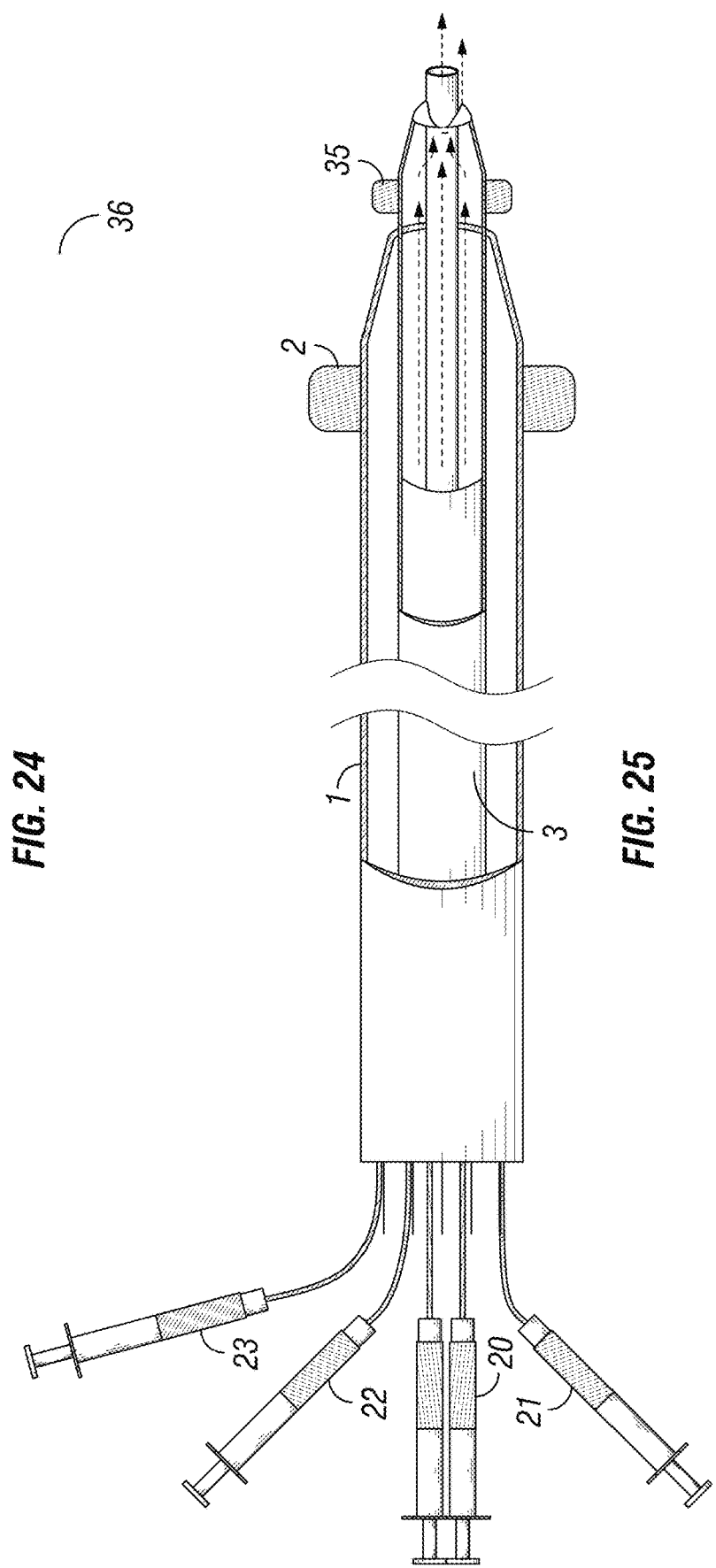
FIG. 24
FIG. 25

ELECTRICALLY CONDUCTIVE HYDROGELS USABLE AS LEAD EXTENSIONS, APPARATUS FOR DELIVERY OF A HYDROGEL INTO THE VASCULATURE, AND METHODS OF TREATING VENTRICULAR ARRHYTHMIA WITH ELECTRICALLY CONDUCTIVE HYDROGELS INJECTED IN THE VENOUS SYSTEM

This application is a U.S. national stage application under 35 U.S.C. § 371 of International Application Serial No. PCT/US2020/049532, filed on Sep. 4, 2020, which claims priority to U.S. Provisional Application Ser. No. 62/896,480, filed on Sep. 5, 2019. International Application Serial No. PCT/US2020/049532 and U.S. Provisional Application Ser. No. 62/896,480 are incorporated by reference herein for all and any purposes.

BACKGROUND

This disclosure relates generally to electrically conductive hydrogels usable as lead extensions and apparatus for delivery of a hydrogel into the vasculature. This disclosure relates more particularly to such hydrogels and apparatus for delivery thereof that are adapted specifically to the treatment of ventricular arrhythmia.

In the United States, sudden cardiac death accounts for more than 350,000 deaths per year. The leading causes of sudden cardiac death are lethal ventricular arrhythmias (VA). The underlying electrophysiologic derangement mechanistically responsible for VA is delayed conduction velocity in scarred or otherwise diseased myocardium (cardiac tissue). Much like a wave hitting a stationary dinghy, a normal heartbeat can be interrupted by a zone of diseased cardiac tissue. And just like the eddy currents formed by the collision of a wave with the dinghy, so, too, eddy currents can be formed by the collision of a normal heartbeat with scarred heart tissue. This process is referred to as "re-entry" and the eddy currents are referred to as "re-entrant wavefronts." Once formed, re-entrant wavefronts rapidly propagate, causing chaotic cardiac activity that leads to loss of organized cardiac contraction, loss of cardiac output, drop in tissue perfusion, and, if left untreated, death within minutes.

The most common cause of cardiac scarring is prior myocardial infarction (MI). Large amounts of scar lead to weakness in cardiac contractility (contraction) with consequent symptoms of congestive heart failure (CHF). Furthermore, the regions of scar also serve as substrate for lethal re-entrant arrhythmias as described above. Thus, scar tissue created in the setting of an MI has two long-term sequelae: First by decreasing the number of viable—and thus contractile—cardiac cells it can lead to symptoms of "pump failure" and second, by increasing the incidence of re-entry, it can lead to arrhythmia. This correlation is so strong that the current guidelines recommend implantation of cardiac defibrillators (ICDs) for all patients with left ventricular ejection fraction (LVEF) less than 35% (normal LVEF≥50%). The medical and economic consequences of this practice cannot be overstated, especially when keeping in mind that a defibrillator offers no improvement quality of life, as its only purpose is to shock the heart once re-entrant arrhythmia occurs. By virtue of its ability to eliminate re-entrant arrhythmia, the technology we are proposing offers the potential for a future in which a large fraction of the thousands of defibrillators implanted annually in the US (and the high cost to the healthcare system associated with the implants) would no longer be necessary. Not only are defibrillators extremely expensive, but also the treatments that they deliver are associated with extensive collateral damage. ICD shocks are extremely painful and occur almost always without warning. Defibrillation shocks have been associated with post-traumatic stress disorder and depression due to these painful and unexpected shocks.

Current options for the prevention of VA are severely limited. Given that the underlying pathophysiology is one of delayed/diseased cardiac electrical conduction, the most obvious treatment strategy is to restore electrical conduction across scarred myocardium. It is believed that no such treatment exists. Instead, much like chemotherapy for the treatment of cancer, the prevention of VA currently consists of medicines with high toxic profiles and low efficacy or destroying more cardiac tissue in the diseased regions via the process of ablation or defibrillation of VA after onset Pharmacological solutions such as antiarrhythmic drugs further slow conduction velocity to prevent a re-entrant wavefront. However, these drugs can be toxic and, in some cases, even pro-arrhythmic. Ablative strategies, although widely adopted, can lead to a recurrent arrhythmia in 18-40% of cases. In certain cases, ablation carries the risk of pericardial effusions and coronary artery occlusions.

Thus, there is a clinical need for improved treatments for these conditions, which hydrogels and apparatus for delivery of a hydrogel into the epicardial venous system would meet. The hydrogel would provide improved cardiac conduction after myocardial infarction and prevent re-entrant arrhythmia, which can result in sudden cardiac death.

BRIEF DESCRIPTION

The disclosure describes an apparatus for delivery of a curable substance into vasculature or an organ. The apparatus may comprise a mixing catheter. The mixing catheter may have a first hollow lumen separated from a second hollow lumen. The first hollow lumen and the second hollow lumen may be joined into an opening at a distal end of the mixing catheter. The apparatus may comprise a mechanism for mixing of precursors of the curable substance flowing in the first hollow lumen and the second hollow lumen. The apparatus may comprise a mechanism to cleave the curable substance from the mixing catheter. The apparatus may comprise a mechanism to anchor the mixing catheter or prevent backflow of the precursors. The apparatus may comprise a mechanism to deliver the precursors. The mechanism to deliver the precursors may be attached to the proximal end of the mixing catheter.

The disclosure also describes a method of delivery of a curable substance. The method may comprise the step of providing the apparatus describe hereinabove. The method may comprise the step of flowing a first precursor of the curable substance in the first hollow lumen. The method may comprise the step of flowing a second precursor of the curable substance in the second hollow lumen. The method may comprise the step of mixing the first precursor with the second precursor to form a mixture. The method may comprise the step of injecting the mixture into vasculature or an organ. The method may comprise the step of connecting a lead of a defibrillator or pacemaker to the mixture. The method may comprise the step of curing the mixture.

The disclosure also describes a biostable, biocompatible, conductive hydrogel for injection into a venous system or an organ. The hydrogel may comprise a crosslinked network formed by hydrophilic macromers. The hydrogel may comprise ions solvated in an aqueous phase of the hydrogel. The hydrogel may comprise conductive elements that are tethered to the crosslinked network through biostable covalent bonds.

The disclosure also describes a method of making a biostable, biocompatible conductive hydrogel for injection into a venous system or an organ. The method may comprise the step of combining a first precursor solution with a second precursor solution. The first precursor solution may comprise crosslinkable hydrophilic macromers, at least one of ions and crosslinkable conductive elements, and a reducing agent. The second precursor solution may comprise crosslinkable hydrophilic macromers, and a free radical initiator. After the first and second precursor solutions are combined, the crosslinkable hydrophilic macromers may form a crosslinked network. If present, the ions may be solvated in an aqueous phase of the hydrogel. If present, the crosslinkable conductive elements may be tethered to the crosslinked network via biostable bonds.

The disclosure also describes method of treating ventricular arrhythmia. The method may comprise the step of injecting the biostable, biocompatible, conductive hydrogel into a venous system of the heart. The method may comprise the step of curing the conductive hydrogel. The method may comprise the step of connecting a lead of a defibrillator or pacemaker to the biostable, biocompatible, conductive hydrogel. The method may comprise the step of delivering current from the defibrillator or pacemaker.

BRIEF DESCRIPTION OF THE DRAWINGS

For a more detailed description of the embodiments of the disclosure, reference will now be made to the accompanying drawings, wherein:

FIG. 2A shows hydrogel injected into a porcine AIV using a dual lumen catheter;

FIG. 2B shows cured hydrogel that was successfully removed from the AIV and ex vivo contrast imaging shows extension into small venous tributaries;

FIG. 2C shows myocardial capture that was achieved as demonstrated by sinus and pacing ECG;

FIG. 3A shows confirmation that the redox agents are cytocompatible at a range of concentrations;

FIG. 3B shows tunable mechanical properties of the hydrogel;

FIG. 5A shows that the addition of silver nanoparticles increased conductivity of the hydrogel specimen;

FIG. 5B shows that this increase in conductivity can be lost due to leaching of the silver nanoparticles;

FIG. 24 illustrates an angled arrangement of two tubes having hollow lumens that can result in turbulent mixing of the precursor solutions;

FIG. 25 illustrates a mechanism for delivering precursor solutions, and injecting and extracting other fluids by means of syringes attached to the introducer sheath and to the mixing catheter;

DETAILED DESCRIPTION

Figure 1:
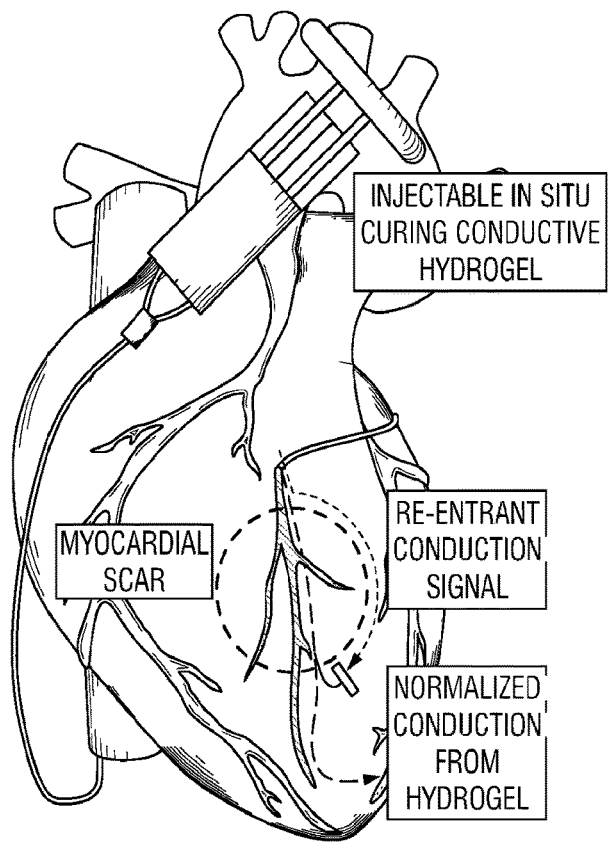
FIG. 1 illustrates a transvenous catheter delivery of the conductive hydrogel to the anterior interventricular vein; the conductive hydrogel can then interface with a standard lead to provide conduction over the scarred myocardium, blocking re-entrant conduction signals.

A conductive hydrogel precursor solution cures after injection into the vasculature of the myocardium. The vasculature acts as a mold for the hydrogel and allows for a pacing signal to be conducted across the myocardium and not at a single point like traditional pacing leads. The catheter-based delivery can accurately place the hydrogels into the myocardial veins and can fill the venous tributaries. In situ crosslinking of the hydrogel precursor solution is achieved through several mechanisms, such as redox initiation by mixing a reducing reagent and oxidizing agent after injection. Conductivity is achieved by doping in conductive polymers or other conductive elements such as ionic species, metallic particles, and/or graphene nanoplatelets. To ensure long-term conductivity, hydrogel macromers may be synthesized without hydrolytically labile groups such as esters, and the conductive elements may be conjugated directly to the hydrogel matrix.

This conductive hydrogel may act as an add-on component of defibrillator or traditional pacemaker leads. A traditional lead can interact with the conductive hydrogel to increase the electrical coverage area. This conductive hydrogel is used to improve the delivery of electric current by the defibrillator or pacemaker leads through increased coverage area.

The hydrogel precursor solution is placed into a catheter. The hydrogel is then injected into the myocardial vasculature where the precursor solution becomes a solid hydrogel network. The vasculature acts as a mold for the hydrogel and allows for the pacing signal to be conducted across the myocardium and not at a single point like traditional pacing leads. The catheter-based delivery can accurately place the hydrogel into the myocardial veins and can fill to the venous tributaries. A defibrillator or traditional pacemaker lead can be inserted, attached, connected, and/or screwed into the hydrogel to allow for contact and propagation of an electric signal. In an alternative method, the pacemaker lead is placed first and the hydrogel is cured around the lead.

Polymerization of the hydrogel can include redox initiation (APS/TEMED, APS/Iron gluconate, Glucose/Glucose oxidase, or any other redox initiation pair), chemical initiation, photoinitiation (Irgacures, Dracurs, or any other photoinitiator), or thermal initiation (AIBN, benzoyl peroxide, potassium persulfate, or any other thermal initiators) among others not listed here. In some embodiments, the polymerization is initiated by the reaction of a reducing agent that is selected from one or more of a hydrocarbon, metal ion, vitamin, enzyme, a ferrous reducing agent, and bioactive agent, with a free radical initiator that is ammonium persulfate, potassium persulfate, or other water-soluble free radical oxidizing initiator.

Other hydrogels that are shear-thinning can also be injected into the vasculature and, with the appropriate shear forces, can reach into the small venous vessels. Other methods of curing can involve an ultraviolet (UV) light that is incorporated into the catheter system in order to provide a curing mechanism for UV-cure hydrogels.

The hydrogel is preferably flexible and tough. The material is preferably able to withstand the repetitive extension and compression placed on the myocardium. The hydrogel would be a long term solution and therefore, the ability to resist fracture and tearing is important. Flexibility may be achieved through using high molecular hydrophilic macromers such as poly(ethylene glycol) to form the hydrogel. Toughness and fracture/wear resistance may be improved through the incorporation of sacrificial secondary interactions such as hydrogen bonds or ionic bonds. As the hydrogel stretches, the sacrificial secondary interactions are broken and reform to allow for resistance to the strain with no or little effect on the permanent hydrogel structure or covalent bonds.

The hydrogel is preferably biostable. To ensure long term use, the macromers used to form the hydrogel are preferably biostable and resist hydrolytic degradation. These characteristics may be achieved by synthesizing hydrogel from macromers without moieties that are susceptible to hydrolysis. Potential hydrogels comprise macromers having a backbone including polyethylene glycols, polyolefin, polyurethanes, poly(urethane ureas), poly(vinyl alcohols), polyamides, gelatin, agarose, hyaluronic acid, collagen, fibrin, and any other hydrogel not mentioned. The macromers may be linear (2 ends) or branched (e.g., 4 arms/ends, 8 arms/ends, etc.). The macromer ends are preferably functionalized with groups such as amide, acrylamide, methylacrylamide, acrylate, methacrylate groups, or other groups. The hydrogel is formed as a crosslinked network of the macromers. This includes covalently crosslinked, physically crosslinked, dual and multiple networks. Additional hydrogen bonding can be introduced into the hydrogel through the addition of monomers or crosslinkers that provide additional physical crosslinking to a network formed by the hydrophilic macromers. Examples of monomer or crosslinker include N-acryloyl glycinamide, methylene bis(acrylamide), 1-Vinyl-2-pyrrolidone, or a combination thereof.

The hydrogel is preferably biocompatible and non-cytotoxic. The hydrogel and byproducts would not cause harm to the local or systemic tissues.

The hydrogel is preferably conductive to allow for propagation of the electrical signal across the myocardium. Conductivity may be conferred through the addition of conductive elements including conductive polymers such as polyanilines, polypyrroles, and polythiopenes or other conductive elements such as metallic nano- or micro-particles, graphene, carbon nanotubes, and ionic solutions (NaCl, KCl, or other salts). To ensure long-term conductivity, the conductive elements may be directly conjugated to the hydrogel network.

This hydrogel enables improved coverage of traditional pacemaker leads. This coverage allows for improved conduction of electrical signals and capture of the cardiac rhythm, enabling pacemakers to be used in previously untreatable populations. In situ curing, conductive hydrogel can be used as a flexible extension to traditional pacemaker leads. The conductive hydrogel is capable of providing the electrical conduction over ischemic myocardium to address the underlying mechanism of re-entrant arrhythmia. The conductive hydrogel is preferably unlike conductive hydrogels developed for biomedical applications, which are biodegradable or do not offer stable conductivity and long-term biostability. It is believed that the conductive hydrogel is unlike currently available conductive hydrogels, which are not available in injectable systems with in situ cure.

The conductive hydrogel is placed across the scar and can provide a conductive pathway across the scar, thereby effectively restoring conduction velocity and eliminating re-entrant circuits. This treatment would effectively eliminate the dinghy mentioned above, as a conductive material laid across the scar would allow the electric wave to pass through uninterrupted.

In other embodiments, the conductive hydrogel placed in such a manner may also reduce the power required when applying electrical shock for defibrillation.

Scarring leading to VA can exist anywhere in the heart, but the current form factor of pacing leads only permits their use in limited locations and areas of capture. Access to smaller vessels and tributaries that cross over scarred regions of the heart would allow capture over large areas of the myocardium. The conductive material can convert previously inaccessible vessels and tributaries to serve as long pacemaker leads with capture across scarred myocardium. The conductive hydrogels offer the unique ability to fill coronary vessels, both large and small, that run along areas of scarring, allowing for novel multisite pacing strategies to treat VA. Referring to FIG. 1, the conductive hydrogel can be injected into coronary veins and tributaries with a transvenous catheter, rapidly cure to provide a flexible pacing lead extension. Once cured, the conductive hydrogel can restore normal conduction over myocardial scarring and/or reduce the energy or voltage required for defibrillation.

Ventricular arrhythmias can also affect those with congenital heart disease. By treating the same underlying cause of re-entrant signals, the hydrogel pacing system can treat patients of any age, including children with congenital heart disease who require ICDs. The utility of the disclosed conductive hydrogels in cardiac applications also extends beyond the treatment of VA. The hydrogels can act as a flexible extension of a pacemaker lead that can track from the epicardial surface, through the mid-myocardial tissue and into the endocardium allowing for pacing multiple sites across the heart. Several clinical applications of multisite pacing, such as improved cardiac resynchronization treatment for heart failure treatment, could also benefit from the disclosed treatment.

Furthermore, the hydrogels can be tailored to individually control the rate of cure after injection and conductance, allowing for a platform technology capable of use in a multitude of biomedical applications. For example, the platform can be used as injectable hydrogels for cell and drug delivery into injured contused spinal cords or traumatic brain injuries that have limited recovery potential due to the development of a cystic cavity surrounded by an inhibitory glial scar. For example, the hydrogel may be delivered into the veins of the brain and may also be injected directly into cerebrospinal fluid, directly on the spine, or directly on the brain (in an open surgical setting). These hydrogels and the delivery method can be tailored for other biological applications.

The relative inefficiency of anti-tachycardia pacing in patients with regions having scarred cardiac tissue is precisely because the pacing impulses cannot penetrate those regions. The size of current pacing leads limits their access to smaller vessels across the ventricle. Utilizing the vasculature as a mold for forming conductive and flexible pacemaker extensions could improve response to current pacing treatments including anti-tachycardia pacing and cardiac resynchronization treatment. Unlike current treatments for ventricular arrhythmia that do not address the underlying pathophysiology, these patient-specific extensions may allow for better capture of the myocardium, enabling improved response to treatment. By effectively restoring conduction velocity and eliminating re-entrant circuits, this treatment can alter the landscape of cardiac rhythm management and prevention of sudden cardiac death. It is believed that no current clinical option can restore conduction across scarred myocardium to address the underlying cause of re-entrant arrhythmias. It is likewise believed that no therapy exists current that can reduce the power applied during defibrillation such that the power levels are below the pain threshold.

The hydrogels described are multifaceted with specific engineered material properties including: injectability, conductivity, and biostability. To date, much of the conductive hydrogel development for biomedical applications has focused on resorbable applications or temporary cell substrates that do not require long-term conductivity. The hydrogels described can bring all of these features together into one working system without losing the functionality of each feature.

In addition, an advanced catheter delivery system can provide a new tool for delivering multi-solution hydrogels. The disclosed design provides of homogenous mixing of the two components for rapid in situ cure while also preventing cure within the catheter that would dislodge the cured hydrogel at the distal end of the catheter upon removal.

It is currently believed that there are no hydrogel formulations or catheter delivery systems that can provide the requisite combination of hydrogel properties and endovascular delivery.

Figure 2A:
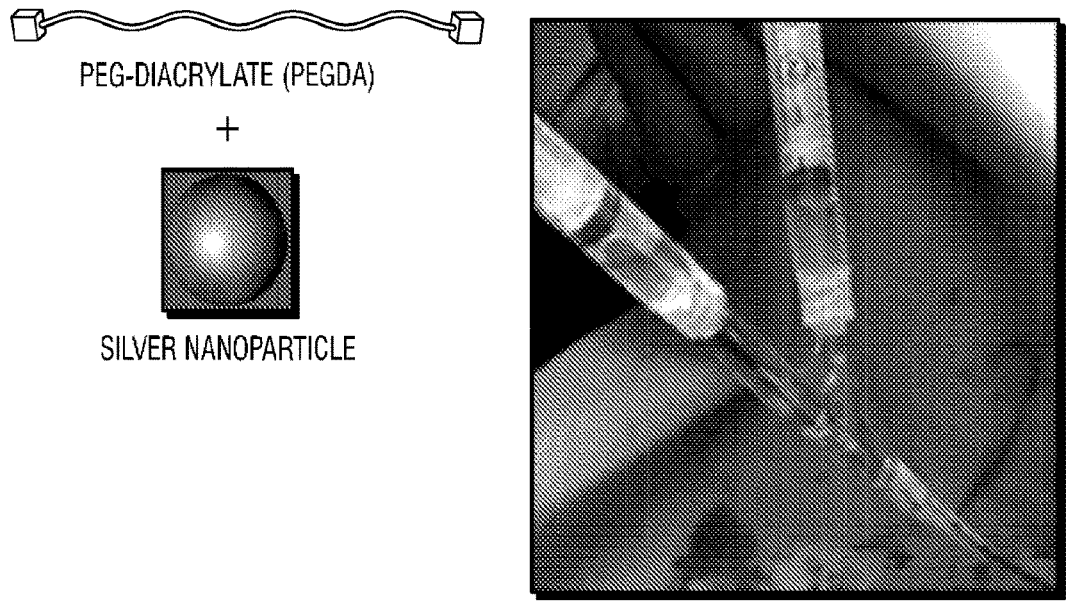
FIGS. 2A-2C illustrate preliminary results of a conductive, in-situ cured PEGDA hydrogel.
Figure 2B:
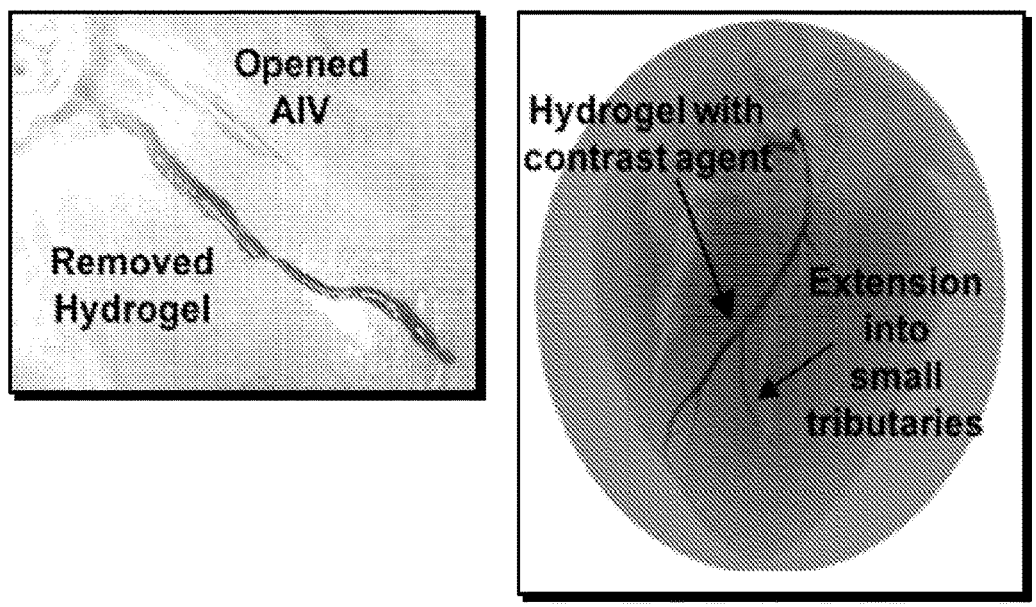
Figure 2C:
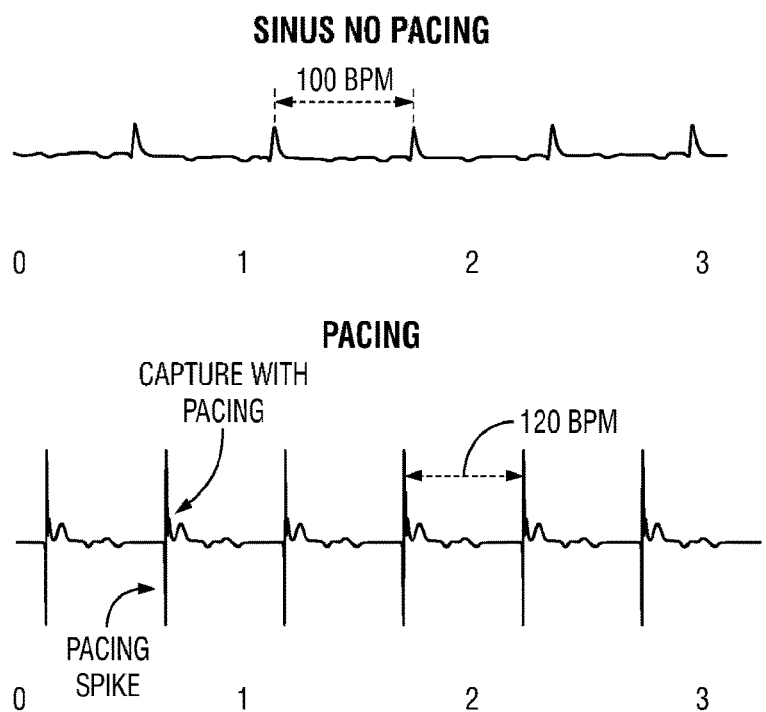

A conductive hydrogel with rapid in situ cure was synthesized. This rapid in situ cure was achieved through redox-initiated free-radical crosslinking of polyethylene glycol diacrylate (10 wt %, 35 kDa) containing 5.5 wt % of silver nanoparticles (15 nm, SkySpring Nanomaterials), coated with polyvinyl pyrrolidone. The hydrogel precursors were injected into the anterior interventricular vein (AIV) of a porcine heart using a dual lumen catheter with one precursor solution containing ammonium persulfate (APS, 11 mM) and one precursor solution containing iron gluconate (IG, 5.4 mM), as shown in FIG. 2A. The hydrogel precursor solutions filled the AIV with extension to small venous tributaries. Mixing of the two precursor solutions resulted in gelation of the hydrogels via redox-initiated crosslinking of polyethylene glycol diacrylate (PEGDA), as shown in FIG. 2B. In situ cured hydrogels containing silver nanoparticles were capable of capturing and pacing the heart compared to hydrogels without silver nanoparticles that had only intermittent capture and no pacing, as shown in FIG. 2C. This study illustrates the feasibility of the disclosed treatment to achieve multisite pacing across the myocardium by converting tributaries into flexible extensions of the pacemaker lead.

The disclosed hydrogel preferably meets several design criteria: (1) rapid in situ cure, (2) conductive, (3) biocompatible, and (4) biostable. Data support the feasibility of using silver nanoparticles to confer conductivity to a polyethylene glycol-based hydrogel that is cured in situ using redox initiation. Surface modification of the silver nanoparticle to conjugate it to the hydrogel matrix may be used to prevent leaching from the hydrogel and loss of conductivity over time. New macromer chemistries may also be synthesized to achieve long-term hydrolytic stability and requisite mechanical properties. The temporal inflammatory and wound-healing response to these novel hydrogel composites may be compared to a negative control (medical grade silicone) as an initial assessment of biocompatibility. Accelerated degradation testing may be used to determine potential effects of degradation on hydrogel conductivity and integrity prior to long term in vivo testing of candidate hydrogels.

Figure 3:
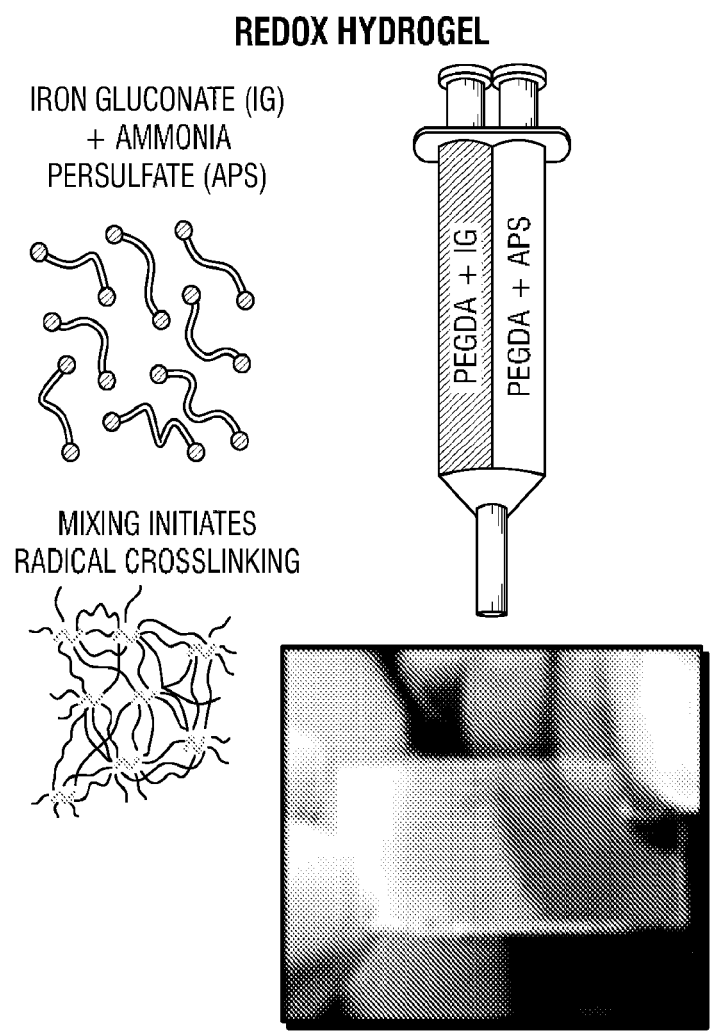
FIGS. 3, 3A-3B illustrate an injectable hydrogel with rapid in situ cure in absence of external stimuli using redox initiation.
Figure 3A:
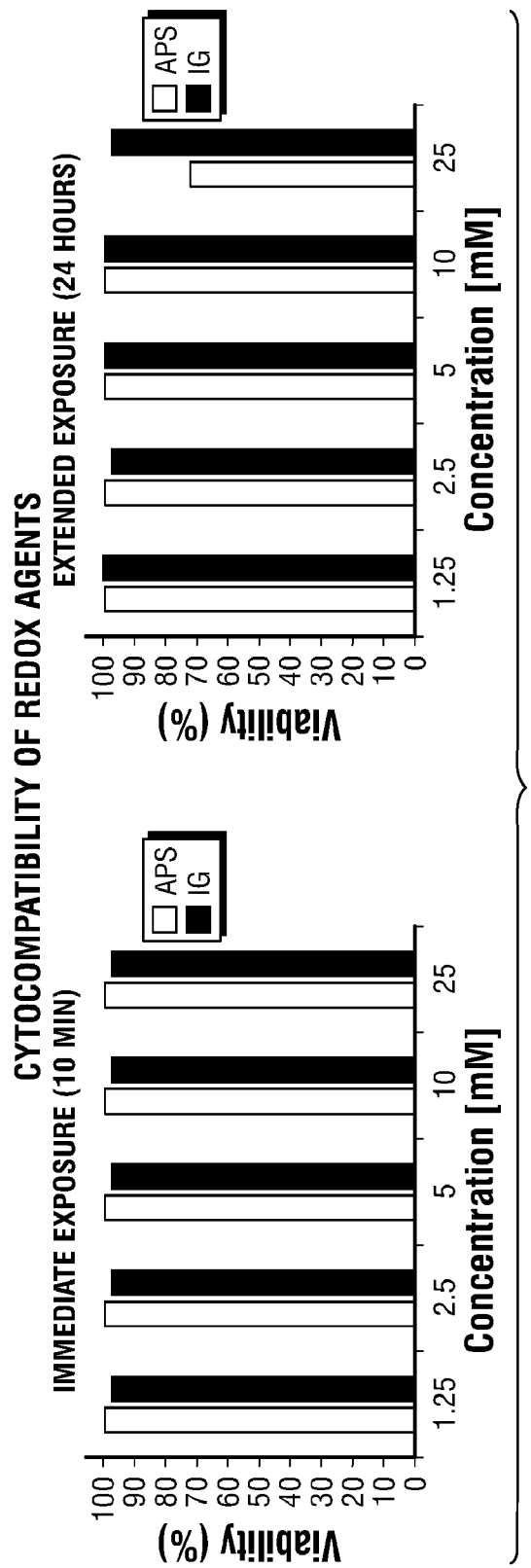

The data in this paragraph provide examples that the redox initiator system is cytocompatible and can be tailored to achieve a range of cure times without external stimuli. An injectable hydrogel system that cures in situ without external stimuli (e.g. UV) may be an important feature for endovascular delivery. A redox-initiated hydrogel system that allows for delivery of the hydrogel solution with rapid in situ cure (less than 5 min) upon mixing of the two components is illustrated in FIG. 3. As a general scheme, a polyethylene glycol diacrylate (PEGDA) aqueous solution containing a reducing agent (iron gluconate, IG) and a PEGDA solution with an initiator (ammonium persulfate, APS) can be loaded into a double-barrel solution and injected through a mixing head to initiate crosslinking. Standard cytocompatibility testing indicated high viability at a range of concentrations of both APS and IG is shown in FIG. 3A. The characterization of the effect of initiator and reducing agent concentrations in this range on cure rate may be obtained using standard rheological testing, and it is possible to tune the cure rate from less than 10 seconds to 10 minutes without detrimental effect on resulting hydrogel properties. In addition to the cytocompatibility of the individual redox agents, encapsulated cells in the redox-initiated hydrogel may be used.

Figure 3B:
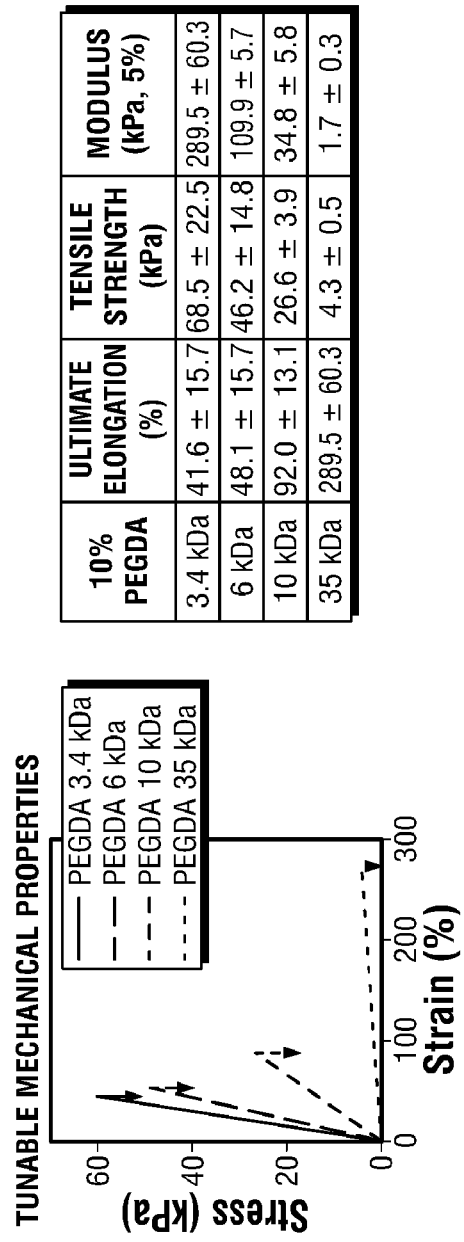

The data in this paragraph provide examples of the broad range of mechanical properties available in the redox hydrogel system. It is possible to tune hydrogel mechanical properties by changing hydrogel composition (e.g. macromer concentration, molecular weight, crosslinker), as shown in FIG. 3B. The mechanical properties of native human myocardium (modulus ranging from 20 kPa to 500 kPa) are preferably selected to tune the hydrogel mechanical properties.

Figure 4A:
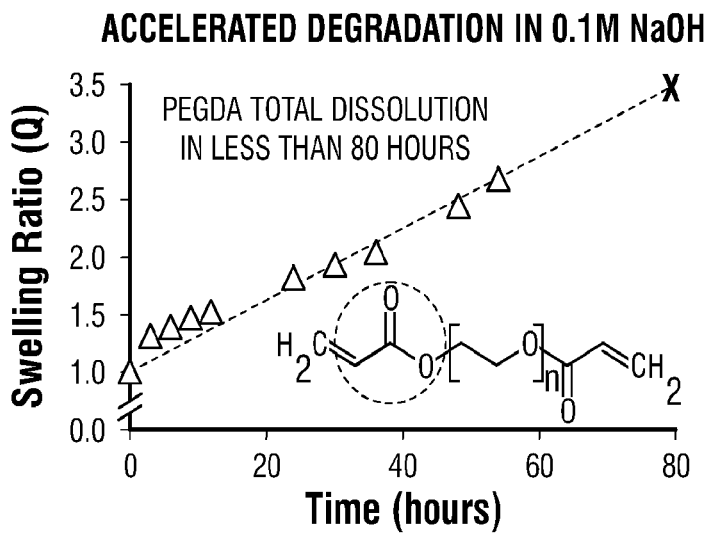
FIG. 4A illustrates accelerated hydrolytic degradation testing that resulted in rapid dissolution of the PEGDA hydrogels and minimal change in the equilibrium swelling of PEGDAA hydrogels.
Figure 4B:
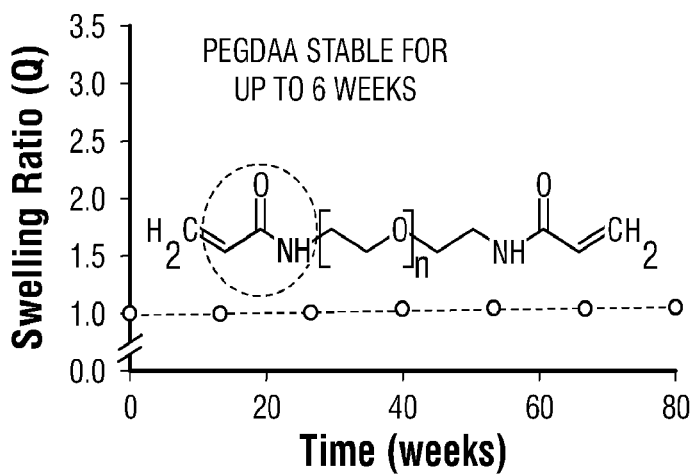
FIG. 4B illustrates the increased biostability of PEGDAA compared to PEGDA confirmed in a subcutaneous rat model.
Figure 4B:
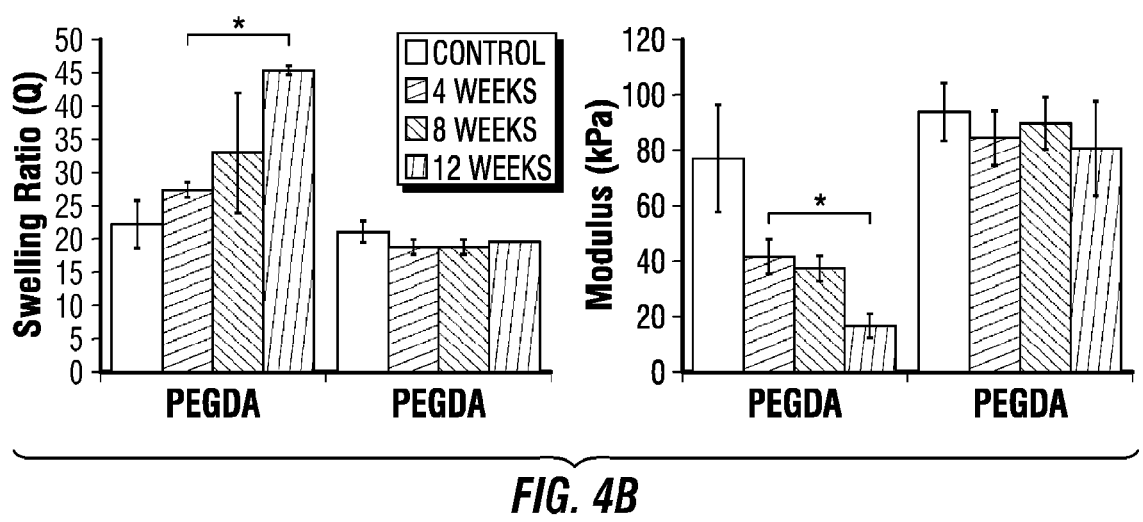

The data in this paragraph provide examples that synthesizing and testing biostable hydrogels is feasible. The primary degradation mechanism of PEGDA hydrogels is likely hydrolytic degradation of the acrylate ester. A biostable hydrogel formulation is needed for permanent devices such as the disclosed treatment. To this end, PEG-diamine macromers (3.4-10 kDa) can be functionalized with acrylamide end groups (PEGDAA) to permit crosslinking according to a protocol adapted from Cosgriff-Hernandez, E.; Hahn, M.; Wilems, T.; Munoz-Pinto, D.; Browning, M. B.; Rivera, J.; Russell, B.; Höök, M., Bioactive hydrogels based on Designer Collagens. *Acta Biomaterialia* 2010, 6, 3963-3977. These hydrogels retained the tunable matrix modulus of PEGDA but displayed dramatically enhanced hydrolytic stability in an accelerated degradation study, shown in FIG. 4A. PEGDA gels fully dissolved within 24 hours in a 0.1 M NaOH solution used to accelerate hydrolysis, whereas the PEGDAA gels showed no statistical difference in swelling or mass loss over 4 wks. To confirm in vivo biostability, PEGDA and PEGDAA hydrogels were implanted subcutaneously in the backs of Lewis rats (n=4) for up to 12 weeks. Increases in equilibrium swelling and decreases in compressive modulus of PEGDA hydrogels after implantation confirmed biodegradation over this 3 month implantation. In contrast, no changes in swelling or modulus of PEGDAA indicated enhanced biostability, as shown in FIG. 4B. A similar strategy can be utilized to generate biostable hydrogels with target mechanical properties.

Figure 5A:
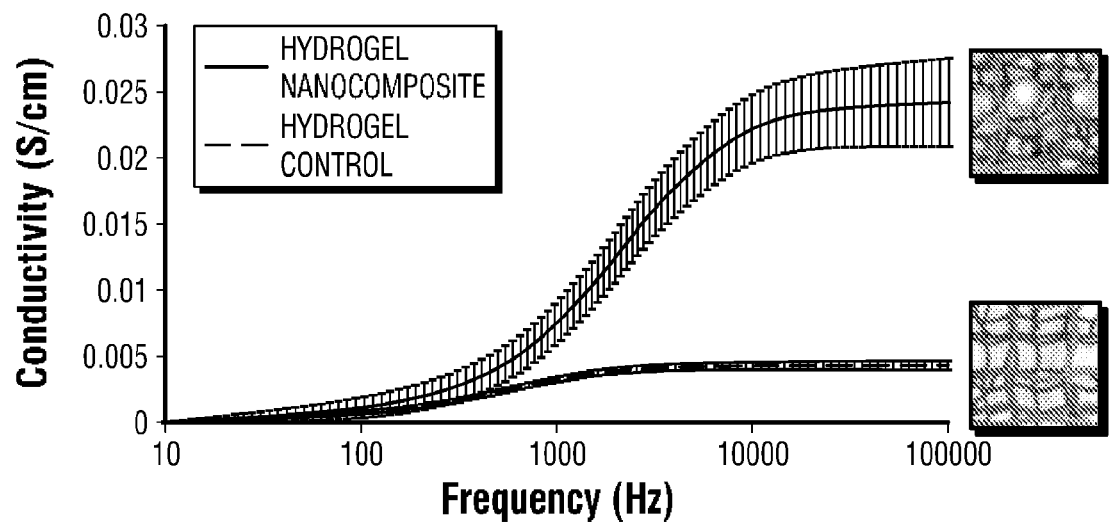
FIGS. 5A-5B illustrate EIS measurements of hydrogel specimens.
Figure 5B:
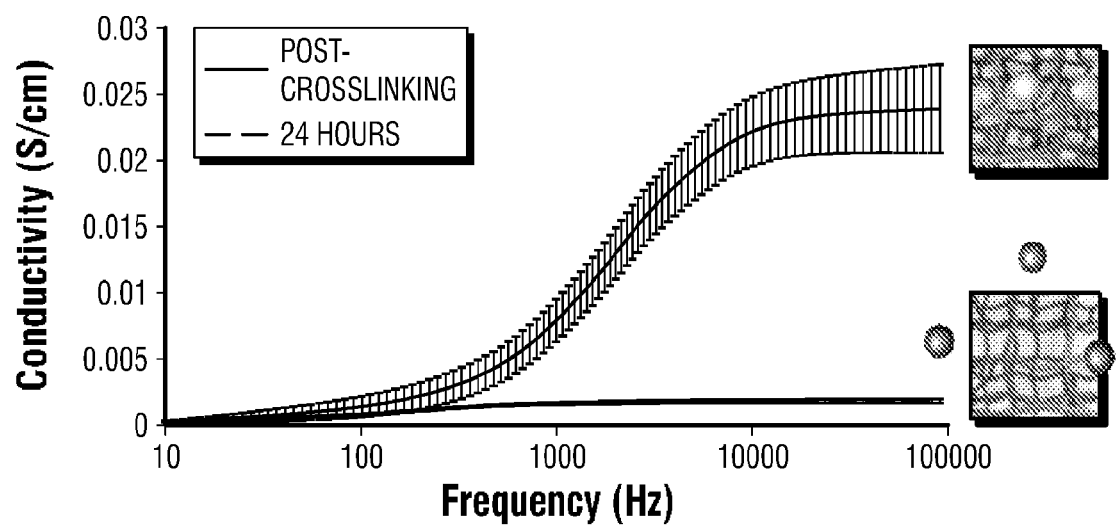

The data in this paragraph provide examples of conductivity testing of hydrogel nanocomposites. A polyethylene glycol diacrylate (10 wt %, 35 kDa) hydrogel containing 5.5 wt % of silver nanoparticles (15 nm, SkySpring Nanomaterials), coated with polyvinyl pyrrolidone, were fabricated and cured using an IG: APS redox pair (APS, 11 mM; IG, 5.4 mM). Electrochemical impedance spectroscopy (EIS) was performed and analyzed, using an impedance analyzer (MTZ-35; Bio-Logic Science Instruments, Knoxville, TN) and the provided MT-Lab software from BioLogic. Hydrogel specimens were placed between two 0.5 inch gold-plated electrodes within a controlled environment sample holder (CESH; Bio-Logic Science Instruments, Knoxville, TN). Prior to testing, sample elements were entered into MT-Lab: radius of the sample, the distance between the electrodes, as well as testing parameters. EIS analysis of each hydrogel specimen was performed by applying an alternative sinusoidal potential of 200 mV in the range of 1 Hz-1 MHz, taking 20 measurements per decade of frequency. The hydrogel nanocomposite displayed an increase in conductivity over the hydrogel control, shown in FIG. 5A. Although the hydrogel nanocomposite displayed promising conductive character, initial hydrogel chemistry selected for ductility had a larger mesh size that was greater than the nanoparticle size and permitted diffusion through the network. The hydrogel specimens were soaked in water for 24 hours to determine the effect of nanoparticle leaching on the hydrogel conductivity. There was a visual leaching of nanoparticles into the solute and a noted decrease in conductivity after 24 hours, shown in FIG. 5B.

Figure 5C:
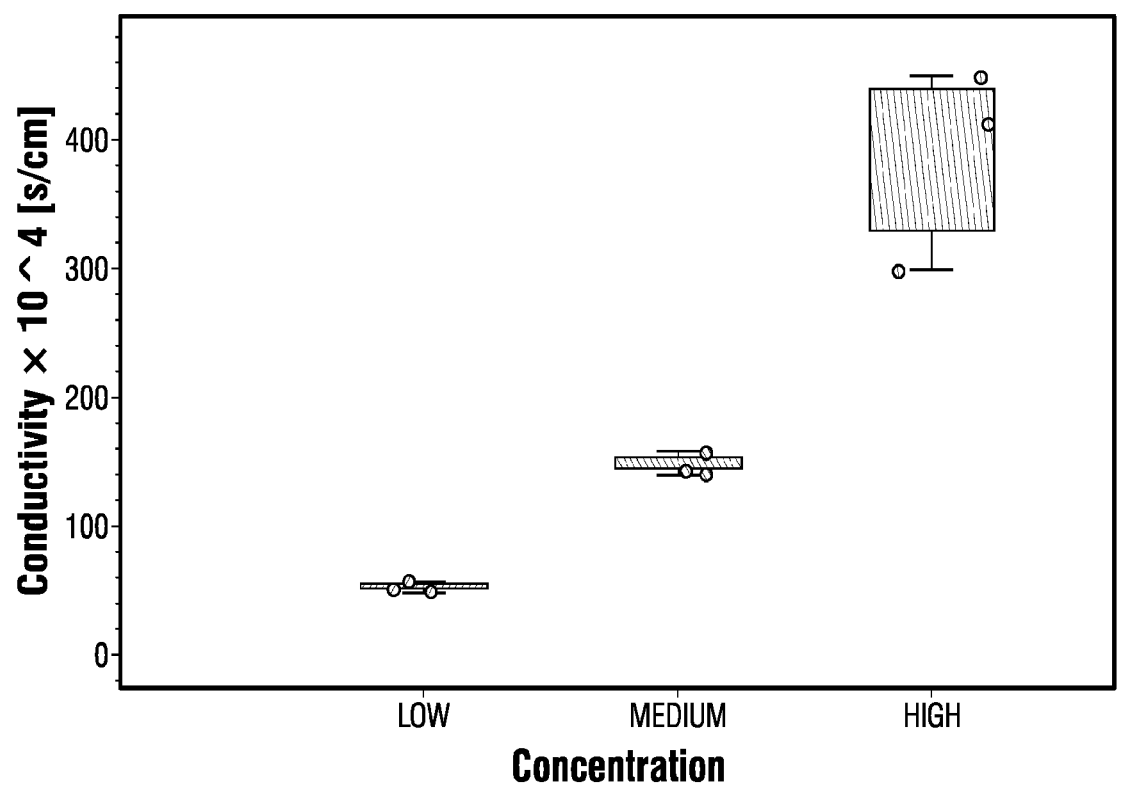
FIG. 5C shows ionic conductivity measurements of hydrogel samples equilibrated in either low, medium or high salt concentration solution.

The data in this paragraph provide examples of conductivity testing of soluble ion-containing hydrogels. Polyethylene glycol diacrylate (10 wt %, 20 kDa) hydrogel slabs were cured using UV light initiation and 0.1 wt % 2-Hydroxy-4'-(2-hydroxyethoxy)-2-methylpropiophenone initiator. Hydrogel slabs were then equilibrated in solutions containing low, medium, or high concentrations of salts, as described in Table 1. Conductivity measurements of hydrogel slabs were performed using a 4-point probe (Keithley 2400 Source meter, Cleveland, OH). Hydrogel specimens were placed on top of a glass slide, and the 4 probes were gently placed on the surface of the hydrogel specimens. Prior to testing, specimen geometry was noted to calculate diameter and thickness correction factors. The analysis was performed by applying a set current between 0-1.0 mAmps and recording the resulting voltage across the probes. To determine conductivity, at least 6 measurements of varying current were used. The ionic hydrogels displayed an increase in conductivity over the deionized water hydrogel control with a corollary increase in conductivity with increasing salt concentrations, as shown in FIG. 5C. The hydrogels displayed a conductive adequate to be useable as lead extensions.

TABLE 1

| | sodium chloride | potassium chloride | potassium phosphate monobasic | sodium phosphate dibasic |
| --- | --- | --- | --- | --- |
| Low | 68.5 mM | 1.35 mM | 0.9 mM | 5 mM |
| Medium | 137 mM | 2.7 mM | 1.8 mM | 10 mM |
| High | 685 mM | 13.5 mM | 9 mM | 50 mM |

Given this conductivity, the hydrogels may also be used to mimic electrical tissues such as myocardium, other muscle, brain, or neurons for the purposes of creating tissue phantoms for research and development purposes.

Synthesis of Hydrogels that Combine Long-Term Conductivity, Biostability, and In Situ Cure.

Figure 6:
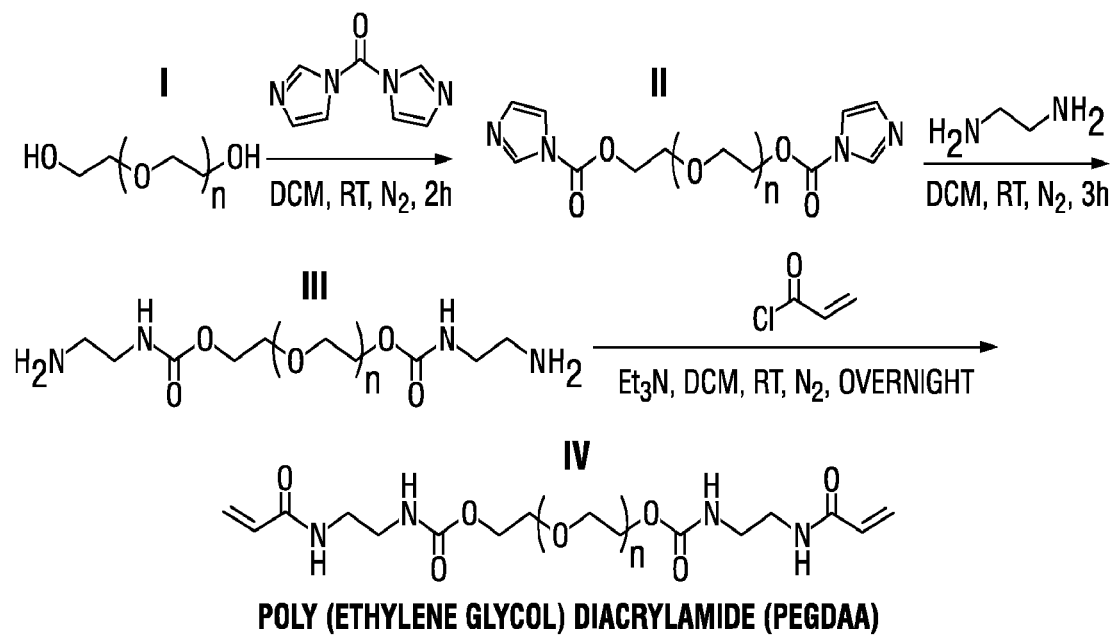
FIG. 6 illustrates a synthesis route to generate biostable PEGDAA macromer for injectable hydrogel.
Figure 7:
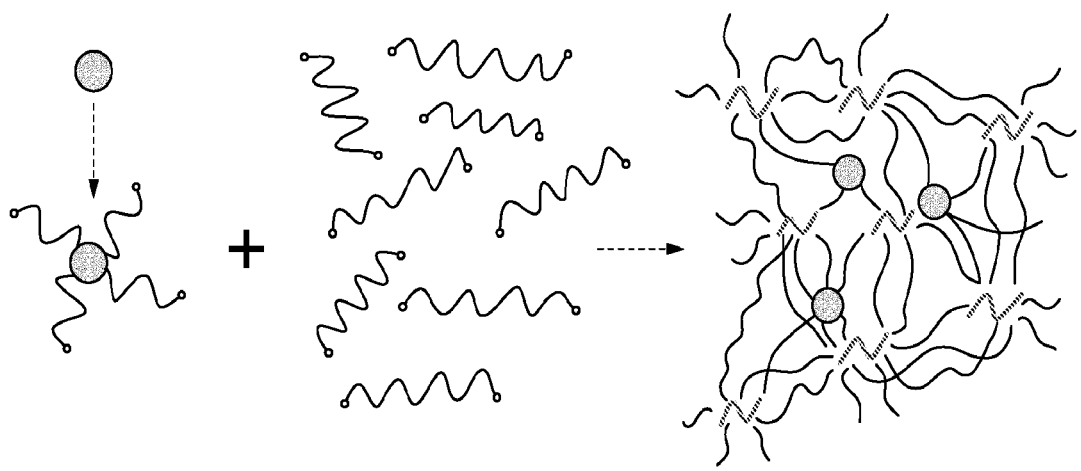
FIG. 7 illustrates nanoparticle modification and conductive hydrogel fabrication, and a testing scheme.

A person of ordinary skill in the art may use a modified nanoparticle to prevent leaching and retain conductivity. For example, in order to synthesize hydrogels that combine long-term conductivity, biostability, and in situ cure, silver or gold nanoparticles, or other biocompatible conducting metal nano particles, may be used as conductive elements in the injectable hydrogel; however, some formulations may display leaching out of the hydrogel matrix which raises concerns with biocompatibility and long-term conductivity. To address this limitation, silver or gold nanoparticles with carboxylic acid functional groups may be used and subsequently functionalized with a PEG diamine (3.4 kDa) using standard carbodiimide conjugation chemistry. Subsequent reaction with acryloyl chloride can introduce stable acrylamide terminal groups that would anchor the nanoparticle into the hydrogel matrix and prevent leaching. To ensure long term biostability of the hydrogel matrix, an alternative PEG macromer may be synthesized that replaces the labile ester groups of PEGDA with stable urethane and acrylamide groups. Briefly, PEG end groups can be initially activated by reaction with 1,1'-carbonyldiimidazol (CDI), then the CDI group can be reacted with ethylenediamine to form urethane linkages, and the end-terminal amines can then be reacted with acryloyl chloride to give an acrylamide-terminated, biostable PEG macromer, as shown in FIG. 6. This synthetic scheme offers several advantages including the introduction of additional hydrogen bonding through the introduction of urethane groups to increase hydrogel toughness. In addition, this scheme permits a broader range of available PEG-diamine molecular weights than available commercially for fabricating PEG diacrylamide.

The effect of hydrogel key compositional variables on the cure rate (IG: 1 mM-10 mM, APS: 5 mM-25 mM), conductivity (nanoparticle concentration from 0.1 to 20 wt %, more preferably from 0.1 to 10 wt %, or ion concentrations from 0.5-1000 mM), and mechanical properties (macromer molecular weight from 0.5 kDa to 100 kDa, more preferably from 10 to 35 kDa, and concentration from 5 to 20 wt %) may be determined using factorial design and established methodology. Hydrogel cure profiles may be characterized by determining gelation onset (crossover of loss and storage modulus) and complete network formation (less than 1% change in complex viscosity) using an Anton Paar MCR 301 rheometer using a parallel-plate configuration heated to 37° C. A target onset of gelation of 1-2 minutes and complete network formation of less than 5 minutes were initially identified from preliminary animal studies. Network formation can be determined by monitoring sol-gel fraction and swelling ratio as a function of redox initiator concentration. A minimum of 95% gel fraction may be set as a success criterion to ensure high conversion. Hydrogel precursor solutions may be cured in a 4 mm diameter plastic tube, and electrochemical impedance spectroscopy may be performed in a faraday cage using a three-electrode potentiostat (AC potential 10 mV, 1 Hz-100 kHz). The conductivity can be calculated using the equation, $\sigma = L/(Z*A)$, where $\sigma$ is the conductivity, Z is the magnitude of impedance, and A is the cross-sectional area of the sample. A target conductivity >$10^{-3}$ S·cm$^{-1}$ was identified from preliminary pig studies that displayed pacing capture. Successful nanoparticle anchoring with minimal leaching (less than 20%) may be evaluated from sol fraction analysis and conductivity measurements before and after Soxhlet extraction for 72 hours. More preferably, successful nanoparticle anchoring with minimal leaching (less than 10%) may be evaluated from sol fraction analysis and conductivity measurements before and after Soxhlet extraction for 24 hours. Target mechanical properties were initially selected based on values of native human myocardium (modulus ranging from 20 kPa to 500 kPa). Design criteria considerations include a hydrogel that would not alter the biomechanical landscape of the myocardium (modulus matching) but also withstand the strains during cyclic loading without fracture. In addition, the pacemaker lead is preferably stably anchored into the hydrogel, without fracture or particulate generation. Tensile and fatigue testing of hydrogel specimens can be completed using protocols established in laboratory. Briefly, ring specimens (2-4 mm long) may be cut from each tubular hydrogel and strained until fracture at a uniaxial strain rate of 6 mm/min using an Instron 3342. Specimen geometry may be selected to prevent slippage. The secant modulus of elasticity, tensile strength, and ultimate elongation may be calculated from the resulting stress-strain data. Fatigue testing may be carried out in a custom environmental chamber with parameters selected to reflect physiological loading. The homogeneity of the candidate hydrogel upon injection may also be tested. The hydrogel precursors can be injected into a tube that simulates the vein using a dual lumen catheter and cured for 24 hours at 37° C. The hydrogel can then be removed from the tube and sectioned in 5 mm specimens. Each specimen can be characterized for gel fraction, equilibrium swelling, nanoparticle concentration, and conductivity, as described above. Finally, the cytocompatibility of the hydrogel composite and leachables may be confirmed using standard serial dilution studies at 24 h, 72 h, and 1 wk with human umbilical vein endothelial cells (HUVECS, Lonza). Results may be used to iteratively guide the selection of the hydrogel formulations until the nanocomposite meets the target combination of properties.

It is preferable that the hydrogels provide both initial target conductivity and sustained conductivity to support long-term functional pacing. An accelerated hydrolysis study may first be used to verify the long-term biostability and conductivity of candidate hydrogel compositions. Briefly, precursor solutions can be prepared with selected initiator or reducing agent concentration, injected into cylindrical tubes, and allowed to cure for 1 hour at 37° C. Specimens (n=10, 8 mm diameter, 2 mm thick) can be tested over a period of 8 weeks in accelerated hydrolysis solution (0.1 M NaOH) with weekly solution changes. The equilibrium volumetric swelling ratio may be calculated as equilibrium swelling mass divided by dry polymer mass and used as a measure of hydrolytic degradation. Electrochemical impedance spectroscopy may then be used to assess the corollary effect on conductivity of the candidate hydrogels over time. Routine iterations of hydrogel nanocomposites may be tested to achieve target properties that display no statistical change after accelerated degradation.

It is noted that the hydrogel mesh size can be greater than the ions that could be used to confer conductivity and could permit diffusion of the ions out of the network. To determine the effect of osmosis on hydrogel conductivity, the hydrogel specimens (cured polyethylene glycol diacrylate (10 wt %, 20 kDa) hydrogel then equilibrated in solutions containing medium concentrations of salts, as described in Table 1) were soaked for one week in 1× Phosphate-Buffered Saline (PBS) solution to simulate physiological conditions. It was found that there was no statistical difference in conductivity after soaking. The conductivity after one week soak was $1.20 \times 10^{-2} \pm 0.27 \times 10^{-2}$ S/cm vs $1.46 \times 10^{-2} \pm 0.09 \times 10^{-2}$ S/cm before soaking.

There may be several criteria for successful hydrogel composition: 1) rapid in situ cure (1-2 min to onset gelation, less than 5 min for complete network formation with a sol fraction less than 5%); 2) conductivity $>10^{-3}$ S·cm$^{-1}$; 3) homogeneity (less than 10% change); 4) mechanical properties to withstand deployment and physiological loading; and 5) no or little statistical change in properties following accelerated hydrolytic testing. A conductance greater than $10^{-3}$ S·cm$^{-1}$ may be sufficient for capture and pacing when the hydrogel is injected into the AIV; however, a conductance values greater than $10^{-3}$ S·cm$^{-1}$ is preferred to account for scarred tissue.

Use of a Hydrogel for Pacing and Confirmation of the Disclosed Treatment.

A hydrogel can be prepared with a contrast agent and the catheter may be primed with the precursor solutions to avoid delivery of air bubbles into the vascular system. The contrast agent is preferably an X-ray contrast agent, such as chelated metal (e.g., tungsten) or functionalized iodine. However, the contrast agent may alternatively be an ultrasound contrast agent, such as nitrogen microbubbles, or a combination of an X-ray contrast agent and an ultrasound contrast agent. A median sternotomy may be performed to expose the heart, and a pacing lead can be placed into the AIV via direct injection into the vein. The pacing threshold can be assessed, in both unipolar and bipolar settings, and the pacing lead can be removed. In the bipolar setting, pacing may be carried out between the distal and proximal electrodes on the lead. The distal electrode and a reference placed on the skin can be used to carry out unipolar pacing. The QRS morphology and width may also be assessed in this baseline state by analyzing the surface ECGs. The lead can be removed and the custom hydrogel catheter can then be inserted into the AIV at the same location. A balloon proximal to the delivery tip can be inflated prior to hydrogel delivery to prevent clearance of the hydrogel from the vein. The delivery and cure may be observed under fluorography, or other imaging techniques, to determine how well the vein is filled and ensure no clearance of the hydrogel. The hydrogel may be allowed to cure for 5 minutes prior to removal of the catheter and fluoroscopic images can be used to confirm that the hydrogel is not dislodged. After removing the catheter, a pacing lead can be placed onto the hydrogel. Impedance can be continuously monitored from the distal electrode of the lead to assess contact between the electrode and hydrogel. The capture threshold may be re-assessed, in both unipolar and bipolar settings. The QRS morphology and width may be measured and compared to the baseline state. The hydrogel should provide a difference in the QRS morphology and a possible shortening of the QRS width.

The hydrogel preferably maintains integrity at the interface with traditional pacing leads, and pacing capture is preferably equal to the capture threshold of the myocardium by using pacing leads in the unipolar and bipolar settings. The hydrogel can elicit a temporal inflammatory and wound-healing response comparable to clinical controls. An absence of statistically significant change in conductivity or equilibrium swelling ratio may be used to establish the initial biostability of the hydrogels and retention of conductivity over time.

Figure 8:
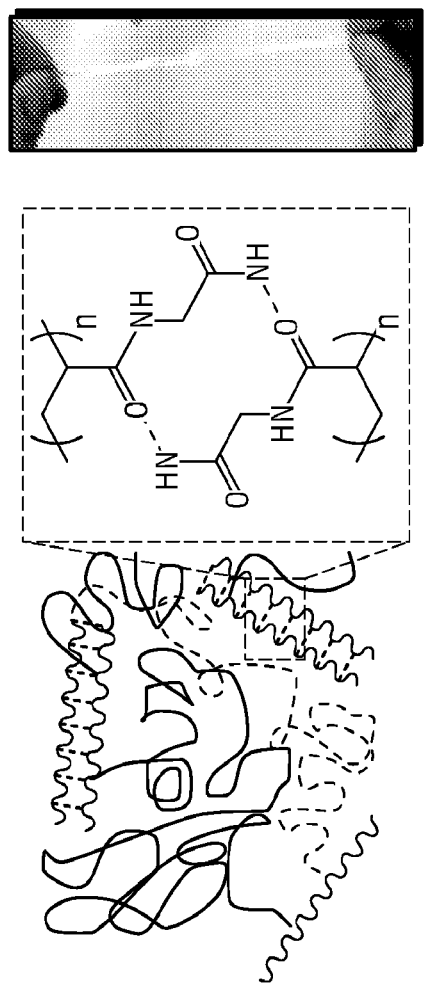
FIG. 8 illustrates an alternate hydrogel chemistry to increase hydrogel toughness using N-acryloyl glycinamide to introduce hydrogen bonding.
Figure 8:
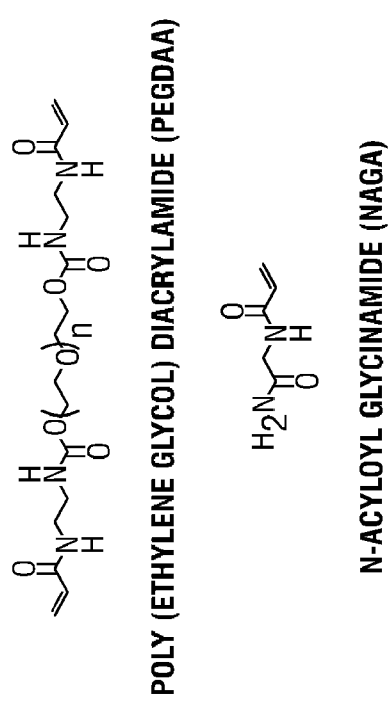

Establishment of key structure-property relationships may be used to identify formulations that can simultaneously achieve the requisite combination of properties for this application through iterative design. The hydrogel system offers numerous mechanisms to tune the resulting hydrogel properties. For example, the cure rate can be iteratively adjusted by varying the APS:IG ratio until target cure rates are achieved. Similarly, the macromer concentration and molecular weight can be adjusted to achieve target mechanical properties. In the event that the hydrogel fails fatigue testing or generates particles during lead anchoring, additional hydrogen bonding can be introduced into the hydrogel through the addition of N-acryloyl glycinamide to increase the toughness, as shown in FIG. 8. Alternatively or additionally to N-acryloyl glycinamide, methylene bis(acrylamide), 1-Vinyl-2-pyrrolidone, other monomer or crosslinker that provides additional physical crosslinking to a network formed by the hydrophilic macromers, or a combination thereof, may be used. The introduction of sacrificial bonds increases defect tolerance and fracture energy. If nanoparticle leaching is observed with corollary loss of conductivity, the number of functionalized linkers can be increased by adjusting the stoichiometry. If necessary, an alternative silver nanoparticle conjugated with branched polyethyleneimine can be used that provides numerous primary amines for subsequent acrylation and anchoring into the hydrogel. In order to increase the conductivity as needed, the hydrogel can be synthesized with macromers that incorporate a conductive aniline trimer and dopant dimethylolpropionic acid into the backbone. Alternatively or additionally, ionic species can be added to the aqueous phase of the hydrogel to increase conductivity, as needed.

Clinically, a pacing lead is commonly placed in a left ventricular (LV) venous branch to provide biventricular pacing treatment. The disclosed treatment for re-entrant arrhythmias utilizes mapping of areas of scar across the myocardium and identification of a suitable venous branch for delivering the hydrogel, and subsequently, a pacing lead. To deliver the hydrogel into the epicardial venous system, a catheter preferably prevents premature cure in the catheter before delivery, allows for controlled delivery of both solutions, ensures mixing of the solutions for a homogeneous resulting material, and a method to control clearance of the solution due to venous return in the cardiovascular system. To this end, the precursor solutions are preferably delivered separately, then mixed at the distal end of the catheter as both solutions fill the veins. Clinically, such a catheter may be delivered through the subclavian vein or through the internal jugular. It is believed that, currently, there are no delivery catheters that can accomplish this goal.

Catheter Delivery System for the Controlled Delivery of the Hydrogel into the Vasculature.

A modified coronary dilation catheter (3.4 Fr, NC Trek, Abbott, Santa Clara, CA) can be used to deliver the hydrogel. However, this catheter design may be limited by the lack of:
1) a way to ensure controlled delivery of both the precursor solutions with equal flow and volume or predetermined flow and volume ratio (such as a double barrel-syringe),
2) a way to control the solution from clearing from the vein due to venous return,
3) a way to ensure homogeneous mixing (such as a mixing head),
4) a reliable mechanism to separate the hydrogel from the catheter after the hydrogel cures in the vein, and/or
5) the ability to steer the catheter to the desired vein for hydrogel filling.

A hydrogel delivery catheter system preferably allows for controlled injection and mixing of the hydrogel precursor solutions to ensure the hydrogel fills and cures in the target vessel. Capture of the myocardium and the pacing parameters may be assessed by pacing directly from the hydrogel.

These results may be compared to pacing using a standard pacing lead placed directly on the myocardium.

Figure 9:
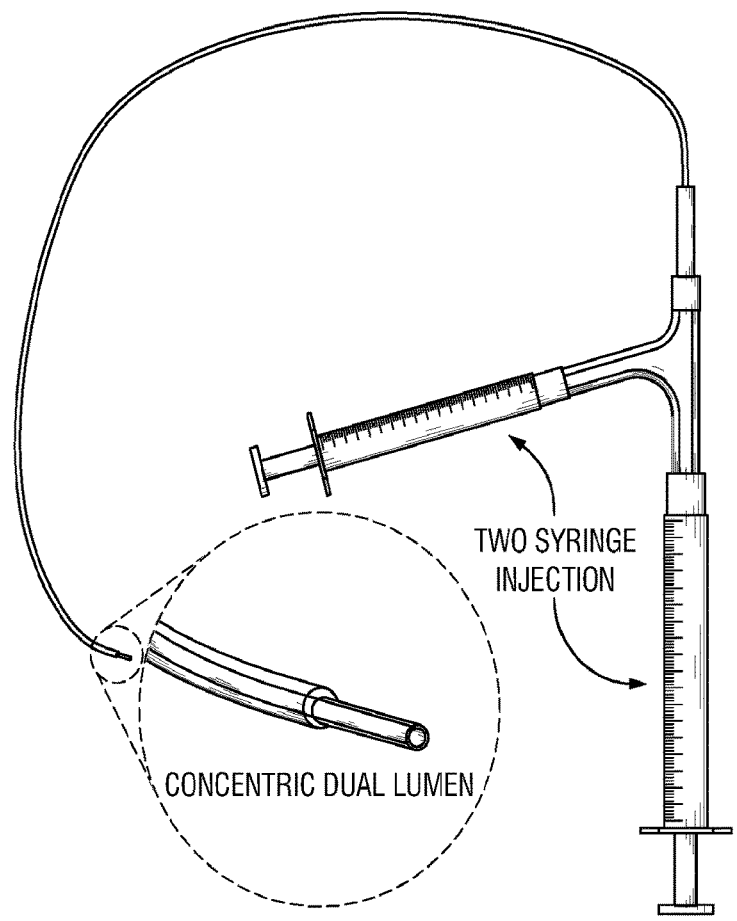
FIG. 9 illustrates a modified angioplasty balloon catheter (2.5 Fr) for hydrogel delivery; the system allows for two different solutions to be injected simultaneously but separately through a concentric dual lumen, with mixing at the end.

A delivery catheter can be made by modifying an NC TREK coronary dilation catheter. The catheter may be cut to approximately 25 cm exposing two concentric lumens. The outer diameter of this portion may be 1.14 mm (3.4 Fr). The outer lumen may serve as an inlet for the balloon, and the inner lumen may serve as a passageway for a thin guidewire (0.014") or fluids such as contrast. In the catheter, the exposed outer lumen may be used for delivering precursor solution containing APS, and the inner lumen may be used for delivering precursor solution containing IG. Once exposed, the outer lumen may be cut using a scalpel 3 mm away from the distal tip. This staggered configuration may ensure that the precursor solutions meets only at the distal end, thus preventing potential back-curing into the catheter. Two syringes may be attached to the open ends on the proximal end to inject the precursor solutions. This catheter system may reliably deliver the hydrogel inside a venous vessel epicardially, as shown in FIG. 9.

Figure 10:
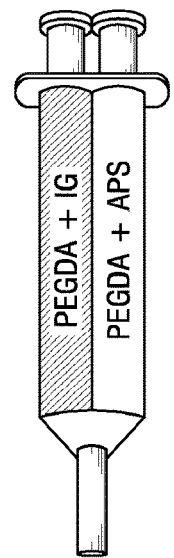
FIG. 10 illustrates a dual syringe that can be used to control the delivery of initiator and reducing agents at equal or predetermined ratio.
Figure 10A:
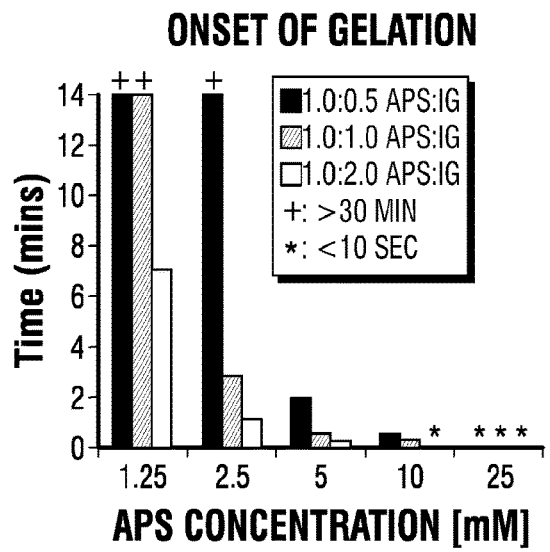
FIGS. 10A and 10B illustrate the effect of initiator concentration and reducing agent ratio on gelation onset and complete network formation of PEGDA hydrogel.
Figure 10B:
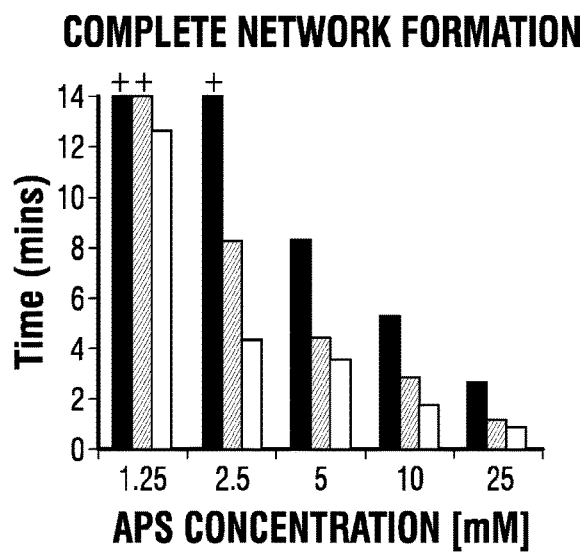

For successful deployment of the hydrogel in the catheter, the hydrogel cure rate is also preferably balanced between rapid cure in the venous vessel without premature cure in the catheter. The cure rate would also allow for sufficient mixing of the precursor solutions to ensure a homogeneous gel in the vessel without venous clearance of precursor solutions. Cure profiles of hydrogel carriers may be characterized by determining gelation onset and complete network formation using an Anton Paar MCR 301 rheometer. Hydrogel precursor solutions may be prepared at an initiator or reducing agent concentration of 1.25, 2.5, 5, 10, or 25 mM, loaded into double-barrel syringes, and injected through a mixing head onto a parallel-plate configuration heated to 37° C. Storage, loss, and complex moduli may be measured every 3 seconds with a 1 mm gap and 0.5% strain. Gelation onset may be determined as the crossing of loss and storage modulus. Complete network formation may be determined as the fourth point after which there is a less than 1% change in complex viscosity. Increasing initiator concentration usually results in more rapid gelation onset ranging from approximately 10 minutes to less than 10 seconds. Uniquely, the use of a ferrous reducing agent may allow for gelation to occur at rates comparable to other APS systems with the benefit of a 10-fold reduction in concentration. Furthermore, complete network formation time can be tuned from approximately 15 minutes to less than 5 minutes, as shown in FIGS. 10A-10B. These key relationships may be used to iteratively adjust the hydrogel cure rate for successful deployment with the new catheter design.

Transvenous Catheter Delivery System to Deploy Hydrogel that Cures In Situ.

Figure 11:
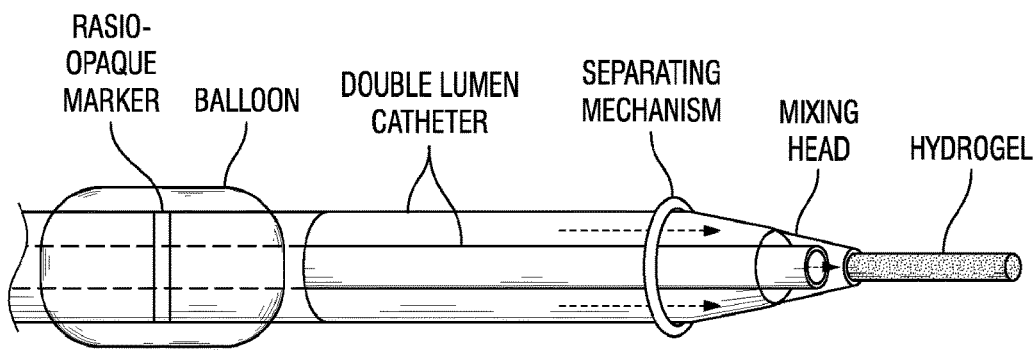
FIG. 11 illustrates a double lumen catheter with mixing head for epicardial delivery of in situ-curing hydrogel.

To deliver the hydrogel into the epicardial venous system, a catheter preferably prevents premature cure in the catheter before delivery, allows for controlled delivery of both solutions, ensures mixing of the solutions for a homogeneous resulting material, controls clearance of the solution due to venous return in the cardiovascular system, and/or provides the ability to steer the catheter to the desired vein for hydrogel filling. To this end, the precursor solutions may be delivered separately, then mixed at the distal end of the catheter as both solutions fill the veins. For example, as shown in FIG. 11, a dual lumen catheter can be used to separate and deliver the precursor solutions. The mixing of the two solutions can be accomplished with a miniaturized mixing head that can be optimized to minimize the length of the mixing head and maximize mixing. Furthermore, the mixing head can be designed to ensure that it is atraumatic to the vessel. The catheter may also have a balloon along its length, proximal to the mixing head. This balloon can anchor the mixing catheter and/or prevent the precursor solutions from clearing due to venous flow. Additionally, a mechanism to deliver the precursor solutions, including a dual injection syringe and a hub, may be used to ensure the solutions are injected at the same flow rate, or at the desired flow rate ratio. Initial qualitative evaluation of proper mixing can be assessed by introducing dye into one of the precursor solutions and injecting the hydrogels via the catheter into a 3 mm (9 Fr) diameter plastic tube; vessel sizes can range from 1.6-4.5 mm. The ability of the balloon to prevent backflow of liquid can be assessed by filling the tube with saline and by holding the tube vertical to ensure a good seal. It is preferably possible to separate the catheter from the hydrogel after the hydrogel is fully cured. This separation may be achieved using a cleaving mechanism. The separation can be tested by allowing the gel to cure around the catheter in the tube, and removal may be determined successful if the hydrogel is not dislodged from the tube as the catheter is removed. This can be confirmed by visual inspection. Hydrogel cure time can be adjusted in order to ensure enough time for sufficient mixing in the tube for a homogeneous gel while also curing quickly enough to prevent precursor solution clearance by venous backflow. This adjusted cure time may ensure reproducible properties for each injection. Furthermore, particulate analysis may be carried out on the cleaving mechanism and the tube testing system. Various locations (e.g., balloon, mixing head) along the catheter can be identified by radio-opaque markers. A standard pacing lead may be interfaced with the hydrogel. Impedance can be continuously monitored to assess the interaction of the electrode with the hydrogel. The lead impedance would usually increase upon touching the hydrogel. Once homogeneity is achieved through iterative design, homogeneity of the hydrogel properties may then be assessed by sectioning the resulting hydrogel longitudinally and measuring equilibrium swelling ratio, sol fraction, nanoparticle fraction, and conductivity, as described herein. A navigation mechanism may be added to the catheter in order to guide the tip to a desired vein or, more generally, to particular areas of the cardiovascular system. This navigation mechanism may include electrodes anywhere on the body of the catheter that may be visualized in an electrophysiology mapping system and a mechanical system to guide the catheter. An UV light may also be incorporated into the catheter system. The UV light is preferably placed at a sufficient distance from the distal tip to initiate UV curing.

Use of Transvenous Catheter Delivery System.

Figure 12:
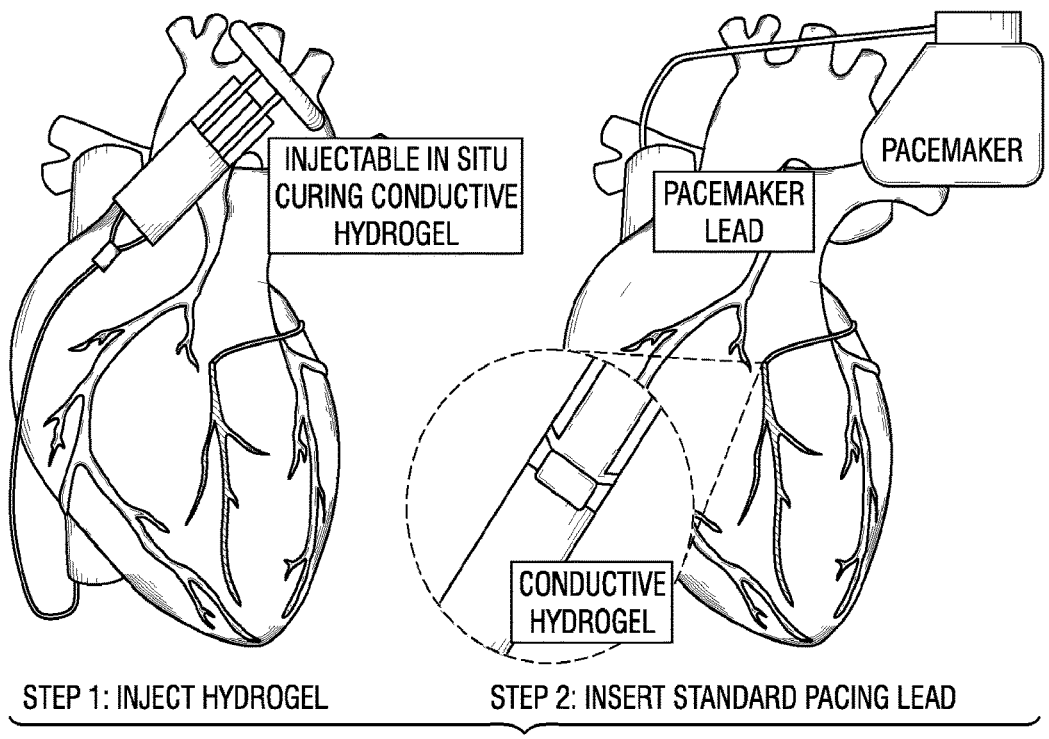
FIG. 12 illustrates a workflow for utilizing the conductive hydrogel to pace across myocardial scar; first, the hydrogel is injected and allowed to cure, then, a traditional pacemaker lead is inserted so that it interfaces with the hydrogel.

The hydrogel may be prepared with contrast, and the catheter may be primed with the precursor solutions to avoid delivery of air bubbles into the vascular system. After, internal jugular vein access is achieved, a pacing lead may be placed into the AIV via a standard introducer sheath placed in the coronary sinus. Pacing threshold may be assessed, in both unipolar and bipolar settings using a Micropace Cardiac Stimulator (Micropace EP, Santa Ana CA), and the pacing lead may then be removed. In the bipolar setting, pacing can be carried out between the distal and proximal electrodes on the lead. The distal electrode and a reference placed on the skin can be used to carry out unipolar pacing. The QRS morphology and width can also be assessed in this baseline state by analyzing the surface ECGs. The lead can be removed and the custom hydrogel catheter can then be inserted through the previously placed sheath. Using fluoroscopic guidance, the catheter can be placed in the AIV and the balloon proximal to the delivery tip can be inflated prior to hydrogel delivery to prevent clearance of the hydrogel from the vein. The balloon can be inflated at approximately the same point that the pacing lead was previously placed and removed. The delivery and cure can be observed under fluorography to determine how well the vein is filled and ensure no clearance of the hydrogel. The hydrogel may cure partially or wholly within another insulative material to focus the conductivity, such as by curing in a stent graft. Curing within a stent graft would provide an insulating outer covering in cases where pacing of certain areas of the cardiac muscle is needed. The hydrogel may be allowed to cure for 5 minutes prior to removal of the catheter and fluoroscopic images before and after removal may be used to confirm that the hydrogel is not dislodged. After removing the catheter, a pacing lead may be placed onto the hydrogel at the proximal end as shown in FIG. 12. Impedance may be continuously monitored using the Micropace system (Micropace EP, Santa Ana CA) from the distal electrode of the lead to assess contact between the electrode and the hydrogel. The capture threshold may be re-assessed, in both unipolar and bipolar settings, as described above. The QRS morphology and width may be measured and compared to the baseline state. A difference in the QRS morphology and a possible shortening of the QRS width should be observable with the hydrogel.

The catheter is preferably able to deliver the hydrogel transvenously in vivo using a 3 to 4 French system (1 to 1.3 mm). Additionally, the hydrogel (mixed with contrast) preferably maintains its mechanical and electrical properties (±10%) when delivered via catheter. The catheter should preferably be removed without removing or dislodging the cured hydrogel as confirmed by X-ray imaging. Preferably, 1) the catheter can be used to deliver the hydrogel to a desired vein and can be removed without pulling out the hydrogel, 2) the hydrogel maintains integrity at interface with traditional pacing leads, and 3) pacing capture is equal to the capture threshold of the myocardium by using pacing leads in the unipolar and bipolar settings.

Instead of a mixing head, other turbulent mixing methods may be embodied in the catheter design. These include the creation of turbulence in each solution using design features such as waves or bumps in the catheter lumens before the solutions mix distally. A dextrose additive may be added to the hydrogel precursor solution to increase viscosity and a standard coronary angioplasty balloon catheter may be advanced to the vein in parallel with the delivery catheter and inflated to block hydrogel clearance. The hydrogel may be injected directly into the vein with an epicardial approach as described herein. A sternotomy may be performed to access the AIV through the epicardium and the pacing lead may be placed at approximately the same location as the baseline lead position.

Thus, a delivery device may comprise an introducer sheath, a mixing catheter, a mechanism to deliver the precursors of the hydrogel attached to the proximal end of the mixing catheter, and a mechanism to cleave the hydrogel from the mixing catheter.

The mixing catheter may include two or more hollow lumens, which may be separated by a wall, and a mechanism for mixing of precursors of the hydrogel. For example, the mixing catheter may comprise a body having a first hollow lumen, and an essentially concentric tube having a second hollow lumen. Alternatively, the mixing catheter may comprise a body having a hollow lumen, a first tube having a first hollow lumen, and a second tube essentially parallel to the first tube, the second tube having a second hollow lumen.

Ports on the proximal end of the mixing catheter may be connected to the mechanism to deliver the precursors of the hydrogel. The mechanism to deliver the hydrogel may include a double barrel syringe, allowing controlled injection of the precursors through the mixing catheter. Alternatively, the precursors may be delivered using one or more separate syringes attached to separate ports on the proximal end of the mixing catheter. Additional syringes or pumps may be attached to the proximal end of the introducer sheath to provide fluid delivery or extraction through the sheath.

The introducer sheath may include a body having a hollow lumen, and a mechanism to anchor the mixing catheter or prevent backflow of the precursors. The mechanism to anchor the mixing catheter or prevent backflow of the precursors may include a balloon along the length of the outer wall.

The mechanism for mixing of the precursors may include ridges, grooves, bumps, or other surface modifications on one or more surfaces of the mixing catheters to introduce turbulence.

Preferably, the mechanism to cleave the hydrogel from the mixing catheter includes a lasso-like member. In other embodiments, the mechanism to cleave the hydrogel from the mixing catheter may include a hydrophobic coating on one or more sides, a flexible material that may return to its original shape after deformation, one or more flaps that can be opened using a pressure driven system. In the mechanism that uses the one or more flaps, the flaps would prevent the hydrogel from sticking to the mixing catheter and hence, the cured substance can be separated. Other mechanisms capable of cleaving the hydrogel from the mixing catheter may alternatively or additionally be provided.

For example, the adjustable lasso-like member may include a loop that can go around the hydrogel, and an actuator to change the size of the loop. In some embodiments, the actuator may include a balloon mechanism attached to the loop that may be inflated or deflated; the inflation of which would increase the size of the balloon. Alternatively, the actuator may include an adjustable wire that may be a part of the loop itself. The wire may be moved back in the distal end of the catheter to reduce the size of the loop.

FIGS. 13-17 disclose a first embodiment of a delivery system whereby the lasso-like member including the loop, advances over a catheter or introducer sheath toward the distal end or tip of the mixing catheter where a material, such as an in situ curing hydrogel, is being delivered. The lasso-like member may be tightened around the material at the distal end of the mixing catheter or introducer sheath, separating it from the remaining material. The loop of the lasso-like member may contain a balloon, which when inflated, may expand the loop such that the system may be retracted over the mixing catheter or introducer sheath once segmentation of the material has occurred. Thus, in use, the lasso-like member can create segments of material exiting a delivery system. The loop of the lasso-like member may be constructed of a more flexible material with the remainder of the lasso-like member housed inside a different, stiffer material forming a casing to aid with advancement of the lasso-like member. The balloon may be attached to the loop of the lasso-like member and may be connected to an air inlet enclosed in the lasso-like member. The balloon may inflate concentrically as to expand the loop. Similarly, the balloon may deflate concentrically as to contract the loop. The distal end of the mixing catheter or introducer sheath may contain a small notch or groove to provide support to the lasso-like member as it is tightened. The distal end of the casing housing the lasso-like member may contain a rubber stopper structure with a small opening to support the lasso-like member during tightening. A secondary lasso-like member may be advanced over the introducer sheath following the advancement and contraction of a primary lasso-like member.

Figure 13A:
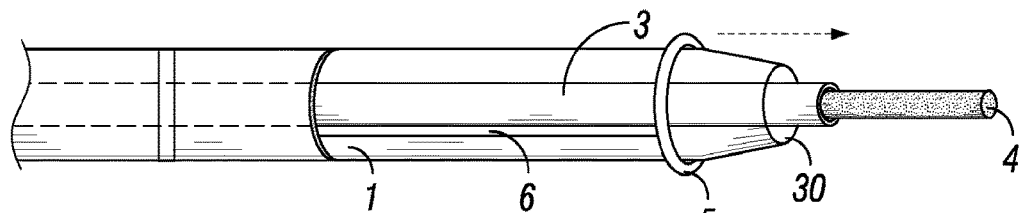
FIGS. 13A-13C illustrate a delivery system including an introducer sheath, a mixing catheter, and a lasso-like member having a loop.
Figure 13B:
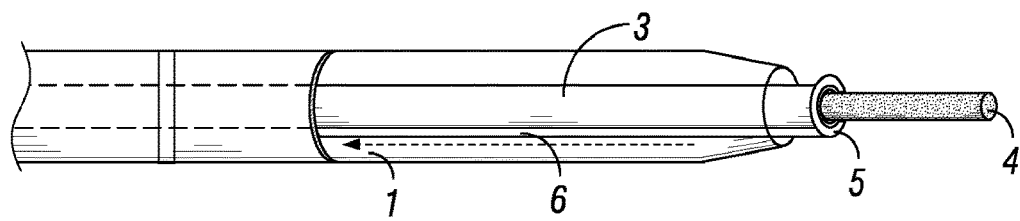
Figure 13C:
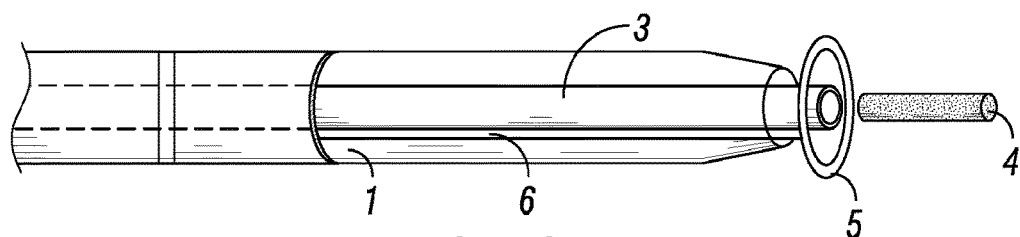

FIG. 13A illustrates an introducer sheath (1) with a hollow lumen (30) which may contain a catheter or a mixing catheter (3) with one or more hollow lumen through which a material, such as an in situ curing hydrogel (4), may be delivered. A lasso-like member includes a wire (5), which includes a loop and a spoke, and a casing (6) surrounding the spoke. The lasso-like member may advance over the introducer sheath (1) to the distal end or end of the mixing catheter (3) where the material (4) may be released. The wire (5), including the spoke and the loop, may be made of a flexible material. The spoke may be housed in a different, stiffer material forming the casing (6). FIG. 13B shows that the wire (5) may be pulled through the casing (6) at the proximal end of the system to tighten the loop, thereby cutting the material (4). FIG. 13C shows that the loop may be expanded after segmenting the material such that it may be retracted over the introducer sheath.

Figure 14A:
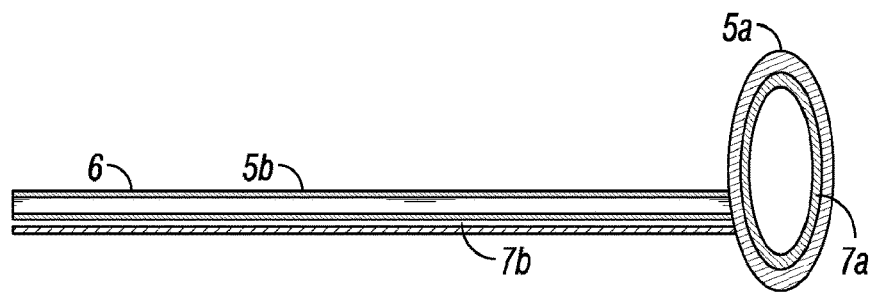
FIGS. 14A and 14B illustrate the loop and the spoke of the lasso-like member shown in FIGS. 13A-13C.
Figure 14B:
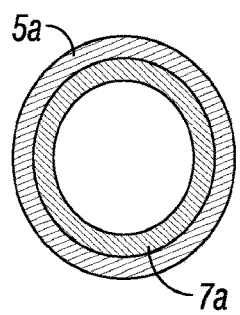

FIGS. 14A and 14B illustrate the lasso-like member including the wire having loop (5a) and a spoke (5b), and the casing (6). The loop (5a), which is attached to the spoke (5b), may include a balloon (7a) to concentrically expand and contract the loop. An air inlet (7b) may be provided through the stiffer casing (6) in the spoke (5b) to deliver and remove air into the balloon.

Figure 15A:
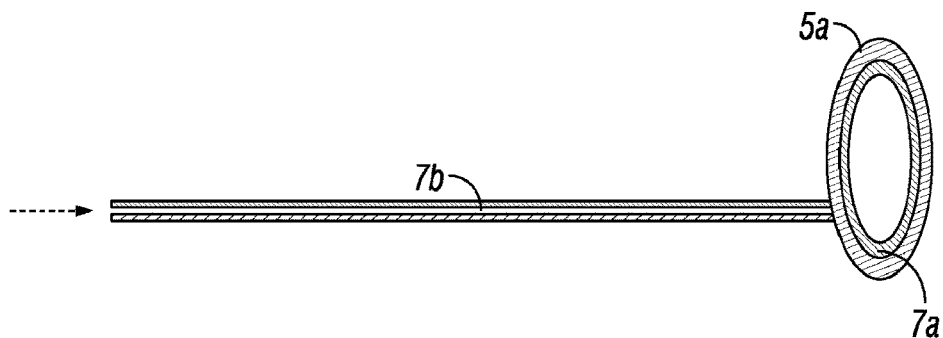
FIGS. 15A and 15B illustrate respectively expanded and contracted configurations of the lasso-like member shown in FIGS. 13A-13C.
Figure 15B:
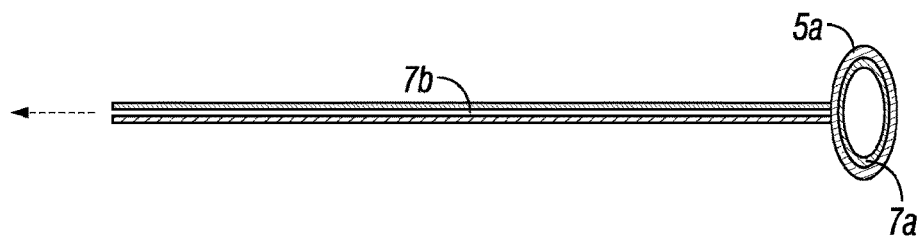

FIG. 15A illustrates that air or another fluid may be delivered into a port of the air inlet (7b), which inflates the balloon (7a), thereby expanding the loop (5a). FIG. 15B illustrates that air or another fluid may be removed through the same port, which deflates the balloon, thereby contracting the loop.

Figure 16A:
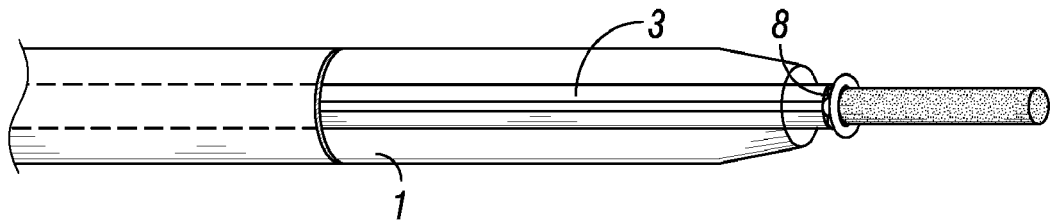
FIGS. 16A and 16B illustrate means for supporting the lasso-like member on a distal end of the mixing catheter shown in FIGS. 13A-13C.
Figure 16B:
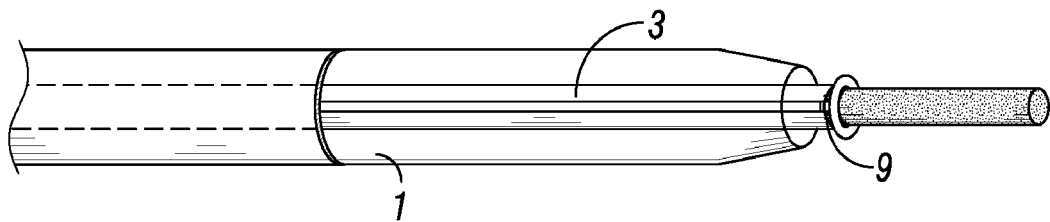

FIG. 16A illustrates that the mixing catheter may be fabricated with a small notch or groove (8) at the distal tip, which may support the lasso-like member as it is tightened. FIG. 16B illustrates that the distal end of the casing of the lasso-like member may contain a rubber stopper (9) with a small opening to support the lasso-like member as it is tightened.

Figure 17A:
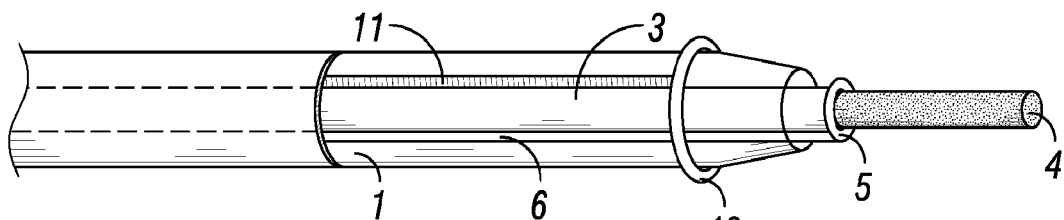
FIGS. 17A-17C illustrate a delivery system including an introducer sheath, a mixing catheter, a primary lasso-like member having a loop, and a secondary lasso-like member having a loop.
Figure 17B:
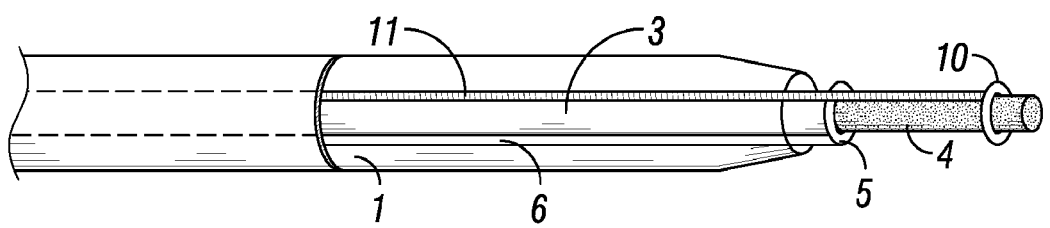
Figure 17C:
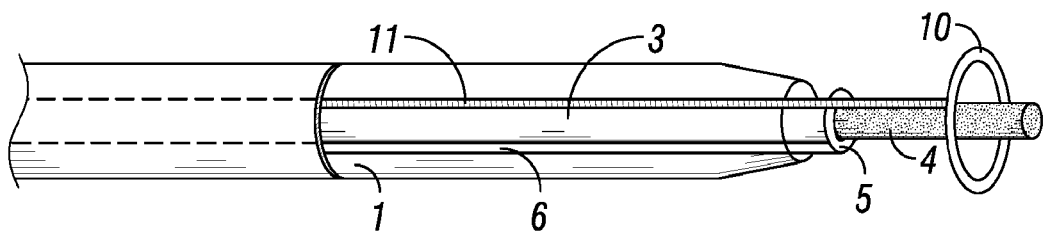

FIG. 17A illustrates a secondary lasso-like member comprising a flexible wire (10) having a loop and a spoke, and a stiffer casing (11), which may be advanced over the introducer sheath (1) once the primary lasso-like member has been contracted. The loop secondary lasso-like member may be advanced to a location beyond the location of the loop of the primary lasso-like member. FIG. 17B illustrates that the secondary lasso-like member may be tightened to create a segment of material. FIG. 17C illustrates that the secondary lasso-like member may be expanded and retracted over the introducer sheath, followed similarly by the primary lasso-like member. The secondary lasso-like member is optional.

In use, the introducer sheath (1) may be advanced to the desired point in a venous vessel or organ. The flexible loop (5a) of a primary lasso-like member may be put around the introducer sheath (1) at the proximal end of the introducer sheath (1). The primary lasso-like member may be advanced over the introducer sheath (1) using the stiffer casing (6) towards the distal end or tip of the introducer sheath (1). A catheter or mixing catheter (3) may be advanced through the lumen (30) of the introducer sheath (1), past the distal end or tip of the introducer sheath (1), where it may deposit material (4). Once the material is deposited, the spoke (5b) may be pulled tight from the proximal end of the system, resulting in the tightening and subsequent segmentation of the material at the distal end of the introducer sheath (1). A notch (8) at the tip of the mixing catheter (3) and/or a rubber stopper (9) at the distal opening of the spoke casing (6) may be provided to support the junction between the spoke and the loop during tightening. Once segmentation has occurred, the loop may expand by way of a balloon system (7a) that may be attached to the lasso-like member. Air or other fluid may be delivered into a port (7b) provided in the lasso-like member to cause expansion of the loop. The lasso-like member may be retracted back over the introducer sheath (1) once the loop is expanded.

If a secondary lasso-like member, including wire (10) and casing (11), is provided, it may be advanced over the introducer sheath (1) past the loop of the wire (5) following the advancement and contraction of the loop of the wire (5). The spoke of wire (10) may be pulled at the proximal end of the system to achieve tightening of the loop of wire (10) and segmentation of a material further away from the loop (5a) of the primary lasso-like member. The loop of the secondary lasso-like member may be expanded following segmentation and may be retracted over the introducer sheath (1). The primary lasso-like member may then segment the material and be retracted.

Figure 18A:
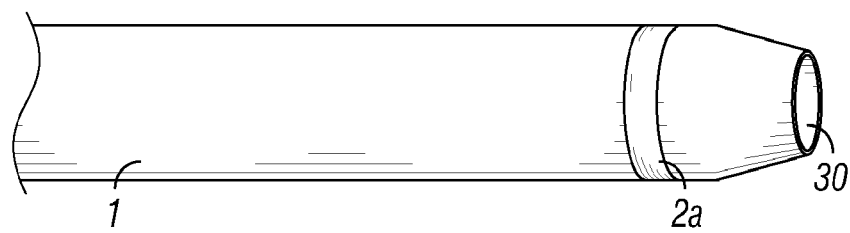
FIGS. 18A-18D illustrate a delivery system including an introducer sheath, a mixing catheter, and the steps of a method to deploy the mixing catheter.
Figure 18B:
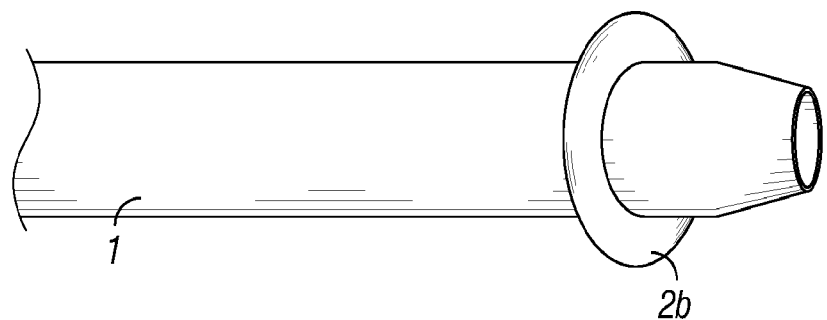
Figure 18C:
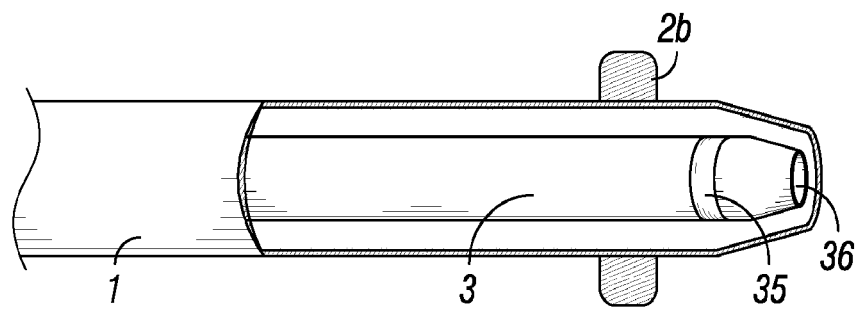
Figure 18D:
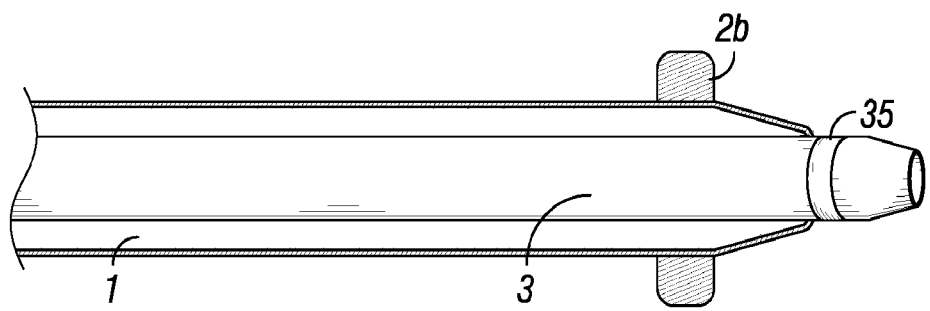

FIGS. 18A-18D illustrate a delivery system that includes an introducer sheath (1) having a body with a hollow lumen (30) and a deflated balloon (2a) located toward its distal end. The deflated balloon (2a) may be inflated (2b) to anchor the introducer sheath (1) and/or to occlude the vessel or the organ in which the introducer sheath (1) is deployed, as shown in FIG. 18B. Suction may be provided through the lumen (30) to evacuate substances from the vessel and/or the organ. Other catheters or materials can be inserted or removed through the lumen (30). For example, the lumen (30) of the introducer sheath (1) may receive a mixing catheter (3), as shown in FIG. 18C. A mixing catheter (3) may comprise of a deflated balloon (35) and a body having two or more hollow lumens (36). As shown in FIG. 18D, the mixing catheter (3) may be advanced past an end opening of the introducer sheath (1) for delivery of fluid or other material, for example, the conductive hydrogel.

Figure 19A:
FIGS. 19A and 19B illustrates a mixing catheter including an inflatable balloon that can be used to anchor the catheter in place or prevent backflow of precursor solutions.
Figure 19B:
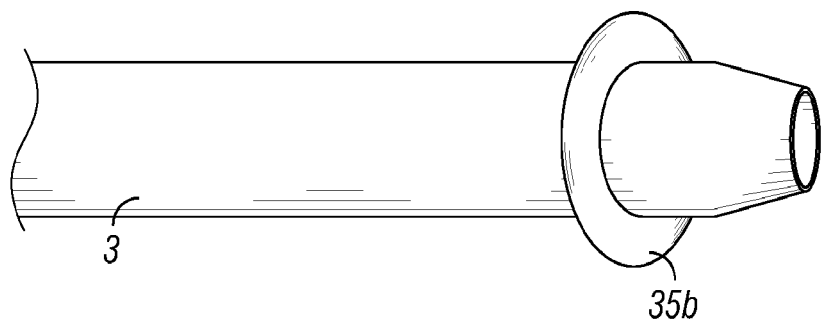

FIGS. 19A and 19B illustrate a delivery system in which a mixing catheter (3) may be used without the introducer sheath (1). In this or other embodiments, the mixing catheter may be provided with a deflated balloon (35a). The deflated balloon (35a) may be inflated (35b) to anchor the mixing catheter and/or the occlude the vessel or the organ in which the mixing catheter is deployed prior to delivery of fluid (or other material), for example, the conductive hydrogel.

Figure 20A:
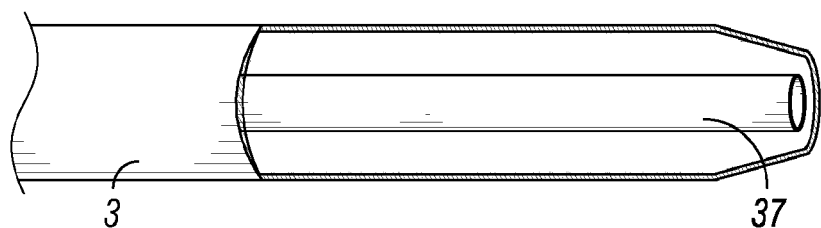
FIGS. 20A and 20B illustrate embodiments of the mixing catheter that comprises two or more hollow lumens separated by a wall to provide precursor solutions while avoiding their mixing through the length of the catheter.

FIG. 20A illustrates a delivery system in which the mixing catheter (3) may contain a single tube (37) for delivery or retrieval of fluid (or other material), for example, one of the precursors of the conductive hydrogel. A wall of the tube (37) separates two hollow lumens, which are essentially concentric.

Figure 20B:
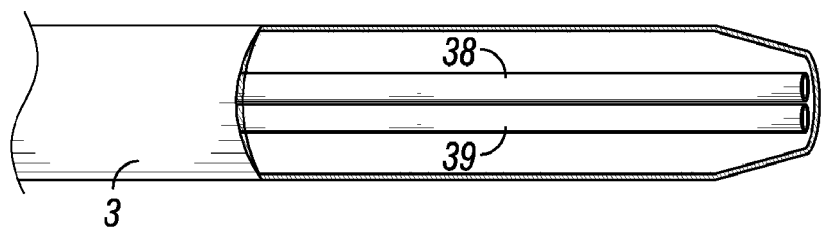

FIG. 20B illustrates a delivery system in which the mixing catheter (3) may contain multiple tubes (38, 39), for delivery or retrieval of fluid (or other material), for example, the precursors of the conductive hydrogel. Each tube (38, 39) includes a hollow lumen. The hollow lumens are separated by the walls of the tubes, and are positioned essentially parallel to one another. Another lumen is provided between the wall of the mixing catheter (3) and the walls of the tubes (38, 39).

FIGS. 21A, 21B, 22A, and 22B disclose embodiments of a delivery system, whereby an end opening of the mixing catheter (3) may be closed with a valve (40a). The flaps of the valve may be elastically biased toward the close position. The flaps of the valve may be opened (40b) by advancing one or more inner tube(s) (37 or 38, 39) inside the mixing catheter (3) or by pushing fluids through the mixing catheter (3). In some embodiments, the valve (40b) can be used to separate the hydrogel outside the mixing catheter (3) from the hydrogel inside the mixing catheter.

Figure 21A:
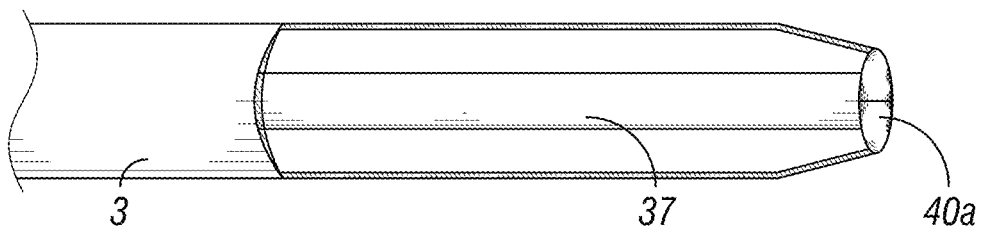
FIGS. 21A and 21B illustrate a cleaving mechanism comprising a flap at the distal end of the mixing catheter, and a method to deliver precursor solutions to the desired location using the mixing catheter with two concentric hollow lumens.
Figure 21B:
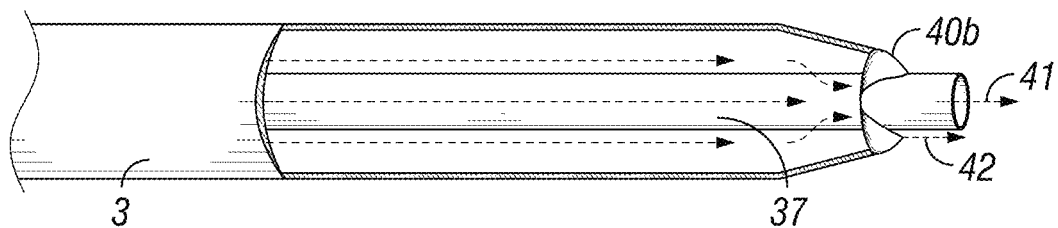

As shown in FIG. 21A, the end opening of the mixing catheter (3) may be closed with a valve (40a). A single inner tube (37) may be located in the hollow lumen of the mixing catheter (3). As shown in FIG. 21B, the flaps of the valve may be opened (10b) by advancing an inner tube (37) past the flaps of the valve. Fluids, for example, the precursors of the conductive hydrogel, can flow within the mixing catheter (3) inside as well as outside the inner tube (37) as indicated by arrows 41 and 42, and thus can be delivered through the mixing catheter (3).

Figure 22A:
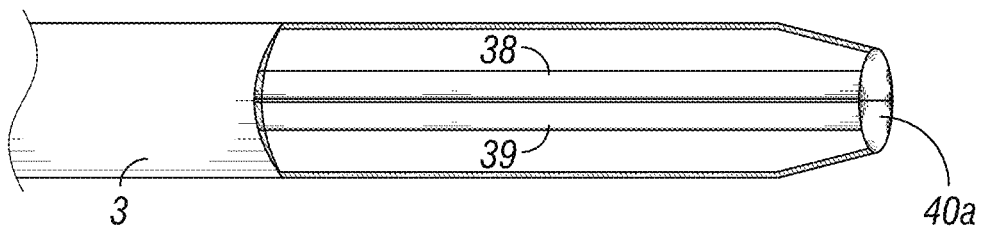
FIGS. 22A and 22B illustrate a cleaving mechanism comprising a flap at the distal end of the mixing catheter, and a method to deliver precursor solutions to the desired location using the mixing catheter with two hollow lumens parallel to each other.
Figure 22B:
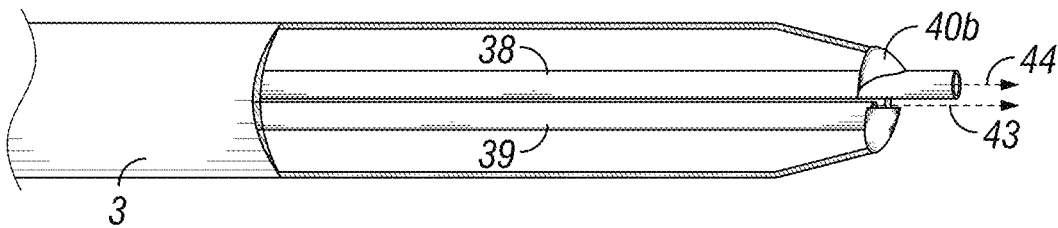

As shown in FIG. 22A, the end opening of the mixing catheter (3) may be closed in a similar manner with valves (40a). Multiple inner tubes (38, 39) may be located in the mixing catheter (3). As shown in FIG. 22B, the flaps may be opened (40b) by advancing one or more of the multiple inner tubes (38, 39). The flaps may be opened by a pressure driven mechanism as well, such as urging fluids through the hollow lumens of the tubes (38, 39). Fluids, for example, the precursors of the conductive hydrogel, can flow inside the inner tubes (38, 39) as indicated by arrows 43 and 44, and thus can be delivered through the mixing catheter (3). Fluids can also flow within the mixing catheter (3) outside the inner tubes (38, 39).

Figure 23B:
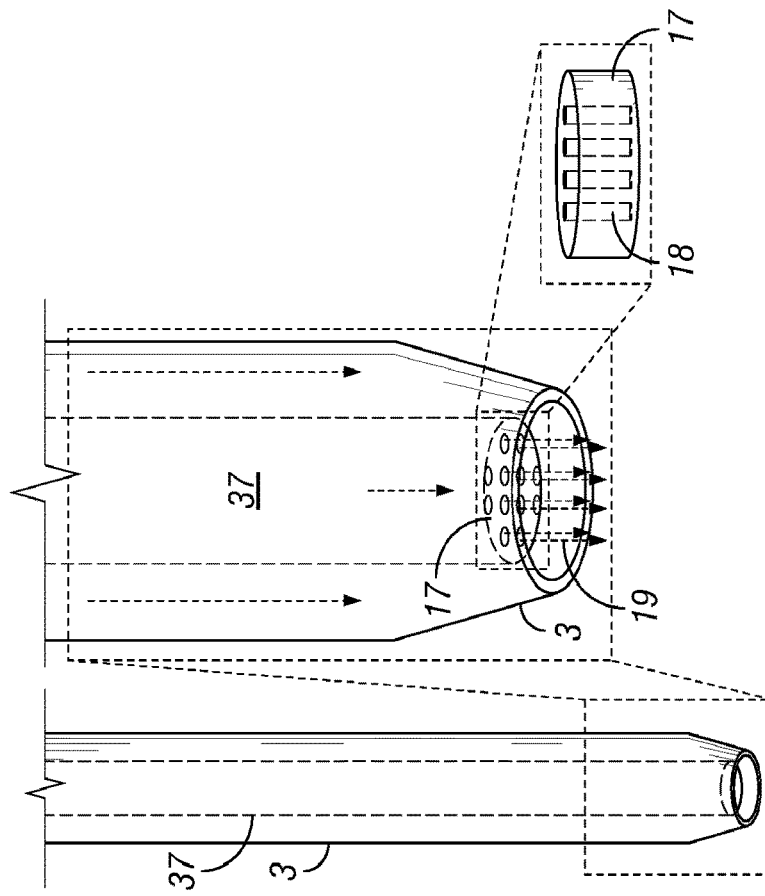
FIGS. 23A and 23B illustrate mixing mechanisms to induce turbulent flow in the precursor solutions prior to mixing.
Figure 23A:
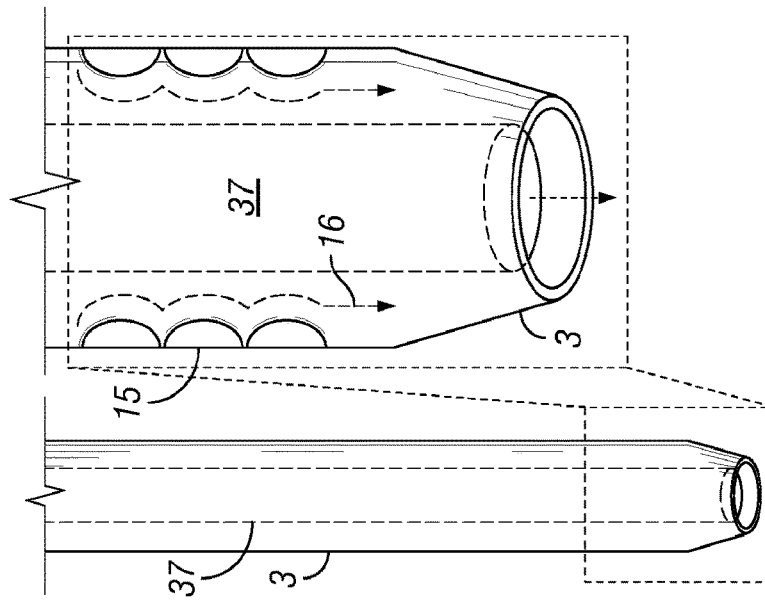

In order to provide mixing of the fluids upon exit of the mixing catheter, bumps, ridges, grooves, or other surface modifications (15) may be placed on the inner surface of the mixing catheter (3), on any surface of a tube, and/or on the surface of any passageway in the mixing catheter, for example as shown in FIG. 23A. The bumps, ridges, grooves, or other surface modifications (15) can create disturbed or turbulent flow (16) of the fluid being delivered. The bumps, ridges, grooves, or other surface modifications (15) are preferably located near a distal end of the mixing catheter (3).

Another way of providing mixing of the fluids upon exit of the mixing catheter (3) may involve placing a mixing head. The mixing head may include a cap (17) with holes (18), twists, or any fenestration at the end of the mixing catheter (3), for example, as shown in FIG. 23B. The holes (18), twists, or fenestration can create flow disturbances or turbulent flow in the exiting fluid (19).

Turning to FIG. 24, mixing of the fluids upon exit of the mixing catheter (3) may also be provided with multiple inner tubes (38, 39) by angling distal portions of the inner tubes toward one another so that when fluid flows out of the inner tubes, they meet and mix. This angling of the inner tubes toward one another may also be accomplished by wrapping or twisting one inner tube around the other.

FIG. 25 illustrates an embodiment of a mechanism to deliver one or more precursors, the mechanism being attached to the proximal end of the mixing catheter (3). In the embodiment shown in FIG. 25, a dual syringe (20) for equal or predetermined ratio flow rates through the mixing catheter. The introducer sheath balloons (2) and mixing catheter balloons (35) may be inflated by syringe injection (21, 22). Fluids could be suctioned through the introducer sheath using another syringe (23). Instead of syringes 20-23, any other fluid delivery/extraction mechanism such as an infusion pump, a vacuum suction, etc., may be used in other embodiments as a mechanism to deliver one or more precursors.

Figure 26:
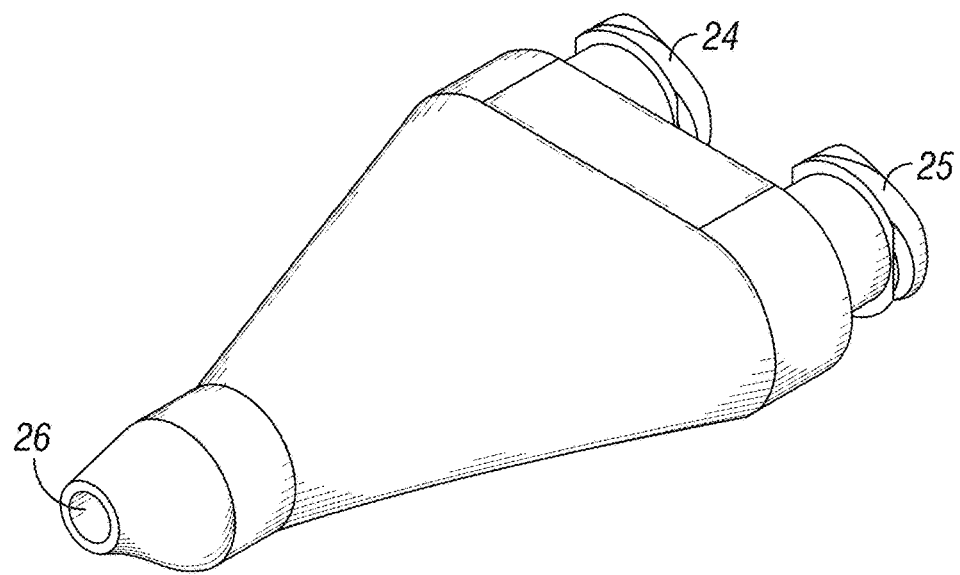
FIG. 26 illustrates a syringe-to-catheter hub, including proximal syringe ports and a distal catheter port.

FIG. 26 illustrates an embodiment of a mechanism to deliver two precursor solutions or other fluids to a mixing catheter that is used to transport the two precursor solutions to a vessel or organ. The mechanism is a syringe-to-catheter hub that comprises inlet ports (24, 25) at the proximal end of the mechanism that are offset from one another. The inlet ports are used for syringe attachment. The distal end of the hub comprises an outlet port (26) to which a mixing catheter including a concentric tube may be connected. The hub is designed to deliver the two precursor solutions or other fluids separately to the mixing catheter and the concentric tube.

Figure 27:
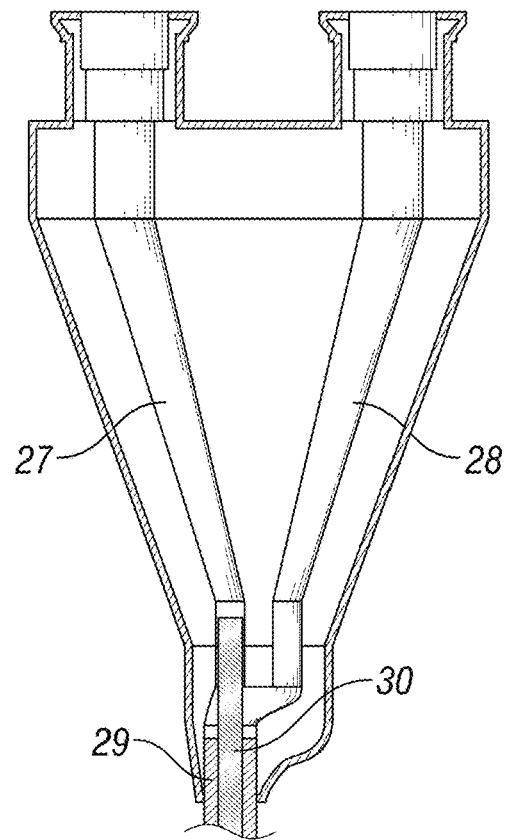
FIG. 27 illustrates the inner channels of the syringe-to-catheter hub.

An embodiment of the inner channels of the fluid hub shown in FIG. 26 are displayed in FIG. 27. The inner channels (27, 28) may coalesce into the outlet port (26) in a coaxial configuration. The proximal end of the mixing catheter (3), for example shown in FIG. 21A, is connected to the inner channel (28), and the inner tube (37), for example shown in FIG. 21A, is connected to the inner channel (27), allowing for the continued separation of precursor fluids throughout the delivery mechanism, from the inner channel (27) to the inner tube (37), and separately, from the inner channel (28) to the space between the inner tube (37), for example shown in FIG. 21A, and the mixing catheter (3), for example shown in FIG. 21A.

Specific embodiments of the invention are shown by way of example in the drawings and description. It should be understood, however, that the drawings and detailed description thereto are not intended to limit the claims to the particular form disclosed, but on the contrary, the intention is to cover all modifications, equivalents, and alternatives falling within the scope of the claims.

What is claimed is:

1. An apparatus for delivery of a curable substance into vasculature or an organ, comprising:
    a mixing catheter having a first hollow lumen separated from a second hollow lumen, the first hollow lumen and the second hollow lumen being joined into an opening at a distal end of the mixing catheter;
    a mechanism to deliver precursors of the curable substance, the mechanism to deliver the precursors of the curable substance being attached to the proximal end of the mixing catheter;
    a mechanism for mixing of the precursors of the curable substance flowing in the first hollow lumen and the second hollow lumen to form the curable substance;
    a mechanism to cleave the curable substance from the mixing catheter, including:
        (i) a lasso-like member comprising a loop, wherein the loop has an expanded configuration and a contracted configuration, and an actuator to selectively move the loop into the expanded configuration or the contracted configuration; or
        (ii) flaps elastically biased toward a close position, the flaps forming a valve; and
    a mechanism to anchor the mixing catheter or prevent backflow of the curable substance.

2. The apparatus of claim 1, wherein the mechanism for mixing includes bumps, ridges, or grooves in one or both lumens of the mixing catheter.

3. The mechanism of claim 1, wherein the mechanism for mixing includes a mixing head at the distal end of the mixing catheter.

4. The mechanism of claim 1, wherein the mechanism for mixing includes tubes having distal portions angled toward one another.

5. The apparatus of claim 1, wherein the cleaving mechanism includes the lasso-like member.

6. The apparatus of claim 5, wherein the actuator includes a concentrically inflatable balloon.

7. The apparatus of claim 5, wherein the actuator includes a spoke surrounded by a casing.

8. The apparatus of claim 5, further comprising means for supporting the lasso-like member on the distal end of the mixing catheter.

9. The apparatus of claim 1, wherein the cleaving mechanism includes the flaps.

10. The apparatus of claim 1, wherein the mechanism to anchor the mixing catheter or prevent backflow of the precursors includes an inflatable balloon on the body of the mixing catheter.

11. The apparatus of claim 1, wherein the mechanism to deliver the precursors comprises a hub having at least two inlet ports offset from one another and a coaxial outlet port, a first inner channel connecting one of the at least two inlet ports to a central region of the coaxial outlet port, and a second inner channel connecting another of the at least two inlet ports to a peripheral region of the coaxial outlet port.

12. The apparatus of claim 11, wherein the mechanism to deliver the precursors further comprises a dual-syringe connected to the at least two inlet ports.

13. The apparatus of claim 1, further comprising a radio-opaque marker to navigate the mixing catheter.

14. The apparatus of claim 1, further comprising an introducer sheath including a body having a hollow lumen sized to pass the mixing catheter, the introducer sheath including an inflatable balloon on the body.

15. A method of delivery of a curable substance, comprising:
providing an apparatus including:
- a mixing catheter having a first hollow lumen separated from a second hollow lumen, the first hollow lumen and the second hollow lumen being joined into an opening at a distal end of the mixing catheter;
- a mechanism to deliver precursors of the curable substance, the mechanism to deliver the precursors of the curable substance being attached to the proximal end of the mixing catheter;
- a mechanism for mixing of the precursors of the curable substance flowing in the first hollow lumen and the second hollow lumen to form the curable substance;
a mechanism to cleave the curable substance from the mixing catheter, including:
  (i) a lasso-like member comprising a loop, wherein the loop has an expanded configuration and a contracted configuration, and an actuator to selectively move the loop into the expanded configuration or the contracted configuration; or
  (ii) flaps elastically biased toward a close position, the flaps forming a valve; and
a mechanism to anchor the mixing catheter or prevent backflow of the curable substance;
flowing a first precursor of the curable substance in the first hollow lumen;
flowing a second precursor of the curable substance in the second hollow lumen;
mixing the first precursor with the second precursor to form a mixture;
injecting the mixture into vasculature or an organ;
connecting a lead of a defibrillator or pacemaker to the mixture; and
curing the mixture.

16. The method of claim 15, wherein the mixture is injected into the venous system of a patient heart.

17. The method of claim 16, wherein the cured mixture is a hydrogel having a conductivity of at least $10^{-4}$ S·cm$^{-1}$.

* * * * *